US008802818B2

(12) United States Patent
Lubell et al.

(10) Patent No.: US 8,802,818 B2
(45) Date of Patent: Aug. 12, 2014

(54) PROSTAGLANDIN-F2 ALPHA RECEPTOR MODULATORS AND USES THEREOF

(76) Inventors: William D. Lubell, Montreal (CA); Sylvain Chemtob, Cote St-Luc (CA); Terence E. Hebert, Pointe-Claire (CA); Audrey Claing, Outremont (CA); Stephane Laporte, Outremont (CA); Carine B. Bourguet, Montreal (CA); Eugenie Goupil, Montreal (CA); Xin Hou, St-Laurent (CA); Danae Tassy, Montreal (CA)

(*) Notice: Subject to any disclaimer, the term of this patent is extended or adjusted under 35 U.S.C. 154(b) by 0 days.

(21) Appl. No.: 13/486,502

(22) Filed: Jun. 1, 2012

(65) Prior Publication Data
US 2012/0309690 A1 Dec. 6, 2012

Related U.S. Application Data

(60) Provisional application No. 61/492,540, filed on Jun. 2, 2011.

(51) Int. Cl.
| | | |
|---|---|---|
| A61K 38/00 | (2006.01) | |
| A61K 38/06 | (2006.01) | |
| C07K 2/00 | (2006.01) | |
| C07K 4/00 | (2006.01) | |
| C07K 5/00 | (2006.01) | |
| C07K 7/00 | (2006.01) | |
| C07K 14/00 | (2006.01) | |
| C07K 16/00 | (2006.01) | |
| C07K 17/00 | (2006.01) | |
| A61K 51/00 | (2006.01) | |

(52) U.S. Cl.
USPC ............ 530/331; 530/333; 514/1.1; 424/1.69

(58) Field of Classification Search
None
See application file for complete search history.

(56) References Cited

FOREIGN PATENT DOCUMENTS

WO          03/104266          12/2003

OTHER PUBLICATIONS

Goupil et al., A Novel Biased Allosteric Compound Inhibitor of Parturition Selectively Impedes the Prostaglandin F2α-mediated Rho/ROCK Signaling Pathway, J. Biol. Chem. Aug. 13, 2010, 285(33):2562425636, published online Jun. 15, 2010.*
Zega and Urleb, Azapeptides, Acta Chim. Slov., 2002, 49, 649-662.*
Dugave and Demange, Synthesis of pseudopeptides containing aza-phenylalanine surrogates of the Phe-pNA motif: Influence on the binding to the human cyclophilin hCyp-18, Letters in Peptide Science, 10:1-9, 2003.*
Andre et al., Aza-peptides 2. X-ray structures of aza-alanine and aza-asparagine-containing peptides. J. Peptide Res. 1997, 49, 556-562.
Anotayanonth et al., Betamimetics for inhibiting preterm labour. Cochrane Database Syst Rev 2004, CD004352.
Boeglin et al., Calcitonin gene-related peptide analogues with aza and indolizidinone amino acid residues reveal conformational requirements for antagonist activity at the human calcitonin gene-related peptide 1 receptor. Journal of Medicinal Chemistry 2007, 50, 1401-1408.
Bourguet et al., Influence of Peptide Mimic Turn Stereochemistry on Allosteric Antagonism at the Prostaglandin F2a Receptor in Peptides 2006, Proceedings of the 29th European Peptide Symposium, K. Rolka, P. Rekowski, J. Silberring Editors, 2006, 436-437.
Bourguet et al., Benzophenone Semicarbazone Protection Strategy for Synthesis of Aza-Glycine Containing Aza-Peptides. Biopolymers, Peptide Science 2008, 90, 824-831.
Bourguet et al., Exploring the relationship between turn geometry and allosteric antagonism of peptide mimic ligands for the prostaglandin F2alpha receptor, Peptides for Youth, The Proceedings of the 20th American Peptide Symposium, Advances in Experimental Medicine and Biology vol. 611, S. E. Del Valle, E. Escher, W. D. Lubell, Editors, Springer Science, New York, 2009, pp. 271-273.
Bourguet et al., Solution-phase submonomer diversification of aza-dipeptide building blocks and their application in aza-peptide and aza-DKP synthesis. Journal of Peptide Science 2010, 16, 284-296.
Brodt-Eppley et al., Prostaglandin receptors in lower segment myometrium during gestation and labor. Obstetrics and Gynecology 1999, 93, 89-93.
Coomarasamy et al., Effectiveness of nifedipine versus atosiban for tocolysis in preterm labour: a meta-analysis with an indirect comparison of randomised trials. Bjog 2003, 110, 1045-1049.
Degrado et al., Polymer-bound oxime esters as supports for solid-phase peptide synthesis. The preparation of protected peptide fragments J. Org. Chem. 1980, 45, 1295-1300.
Duchateau et al., Comparison between atosiban and nicardipine in inducing hypotension during in-utero transfers for threatening premature delivery. Eur. J. Emerg. Med. 2010, 17, 142-145.
Edwards et al., Peptides as drugs. Qjm-an International Journal of Medicine 1999, 92, 1-4.
Goldenberg et al., Preterm birth 1—Epidemiology and causes of preterm birth. Lancet 2008, 371, 75-84.
Goodwin et al., Treatment of preterm labor with the oxytocin antagonist atosiban. Am. J. Perinatol. 1996, 13, 143-146.
Gosselin et al., An Olefination Entry for the Synthesis of Enantiopure a,w-Diamino-dicarboxylates and Azabicyclo[X. Y.0]alkane Amino Acids. J. Org. Chem. 1998, 63, 7463-7471.
Gosselin et al., Rigid dipeptide surrogates: Syntheses of enantiopure quinolizidinone and pyrroloazepinone amino acids from a common diaminodicarboxylate precursor. J. Org. Chem. 2000, 65, 2163-2171.
Goupil et al., A Novel Biased Allosteric Compound Inhibitor of Parturition Selectively Impedes the Prostaglandin F2 alpha-mediated Rho/ROCK Signaling Pathway. J. Biol. Chem. 2010, 285, 25624-25636.

(Continued)

*Primary Examiner* — Maury Audet
*Assistant Examiner* — Joseph Fischer
(74) *Attorney, Agent, or Firm* — Goudreau Gage Dubuc; S. Serge Shahinian; Alain Dumont

(57) ABSTRACT

Prostaglandin-F2 alpha (PGF2α) receptor (FP) modulators of formula I, as well as the use of PGF2α receptor modulators for the treatment of conditions associated with FP activity such as preterm labor and colorectal cancer, are disclosed.

7 Claims, 12 Drawing Sheets

(56) References Cited

OTHER PUBLICATIONS

Haas et al., Tocolytic Therapy—A Meta-Analysis and Decision Analysis. Obstetrics and Gynecology 2009, 113, 585-594.

Hack et al., Outcomes in young adulthood for very-low-birth-weight infants—Reply. N. Engl. J. Med. 2002, 347, 142-142.

Halab et al., Probing opioid receptor interactions with azacycloalkane amino acids. Synthesis of a potent and selective ORL 1 antagonist. J. Med. Chem. 2002, 45, 5353-5357.

Higby et al., Do tocolytic agents stop preterm labor—a critical and comprehensive review of efficacy and safety Am. J. Obstet. Gynecol. 1993, 168, 1247-1259.

Hirst et al., Delay of preterm birth in sheep by THG113.31, a prostaglandin F-2 alpha receptor antagonist. Am. J. Obstet. Gynecol. 2005, 193, 256-266.

Hummel et al., Translating peptides into small molecules. Mol Biosyst 2006, 2, 499-508.

Iams et al., Preterm birth 2—Primary, secondary, and tertiary interventions to reduce the morbidity and mortality of preterm birth. Lancet 2008, 371, 164-175.

Kaiser et al., Peptide and protein synthesis by segment synthesis-condensation. Science 1989, 243, 188-192.

Kenakin, Ligand Detection in the Allosteric World. J. Biomol. Screen 2010, 15, 119-130.

King et al., Calcium channel blockers for inhibiting preterm labour; a systematic review of the evidence and a protocol for administration of nifedipine. Aust. N. Z. J. Obstet. Gynaecol. 2003, 43, 192-198.

Lee et al., Role of azaamino acid residue in beta-turn formation and stability in designed peptide. J. Peptide Res. 2000, 56, 35-46.

Lee et al., The beta-turn preferential solution conformation of a tetrapeptide containing an azaamino acid residue. Journal of Molecular Structure 2001, 569, 43-54.

Linder et al., (S)-3-(tert-Butyloxycarbonylamino)-4-phenylbutanoic acid. Organic Syntheses 2002, 79, 154.

Lombart et al., Rigid dipeptide mimetics: Efficient synthesis of enantiopure indolizidinone amino acids. J. Org. Chem. 1996, 61, 9437-9446.

Marshall, The art of induction/augmentation of labor. J Obstet Gynecol Neonatal Nurs 1985, 14, 22-8.

Martin et al., Annual summary of vital statistics—2003. Pediatrics 2005, 115, 619-634.

McCORMICK, The contribution of low birth-weight to infant-mortality and childhood morbidity. N. Engl. J. Med. 1985, 312, 82-90.

Mittendorf et al., Is tocolytic magnesium sulphate associated with increased total paediatric mortality? Lancet 1997, 350, 1517-1518.

Olson, The role of prostaglandins in the initiation of parturition. Best Practice & Research in Clinical Obstetrics & Gynaecology 2003, 17, 717-730.

Papatsonis et al., Oxytocin receptor antagonists for inhibiting preterm labour. Cochrane Database Syst Rev. 2005.

Peri et al., THG113: A novel selective FP antagonist that delays preterm labor. Seminars in Perinatology 2002, 26, 389-397.

Polyak et al., Rigid dipeptide mimics: Synthesis of enantiopure 5- and 7-benzyl and 5,7-dibenzyl indolizidinone amino acids via enolization and alkylation of delta-oxo alpha,omega-di- N-(9-(9-phenylfluorenyl))amino azelate esters. J. Org. Chem. 1998, 63, 5937-5949.

Presland, Identifying novel modulators of G protein-coupled receptors via interaction at allosteric sites. Current Opinion in Drug Discovery & Development 2005, 8, 567-576.

Rich-Edwards et al., Birth weight and risk of cardiovascular disease in a cohort of women followed up since 1976. British Medical Journal 1997, 315, 396-400.

Russell et al., Cost of hospitalization for preterm and low birth weight infants in the United States. Pediatrics 2007, 120, E1-E9.

Sabatino et al., Exploring Side-Chain Diversity by Submonomer Solid-Phase Aza-Peptide Synthesis Org. Lett. 2009, 11, 3650-3653.

Slattery et al., Preterm delivery. Lancet 2002, 360, 1489-1497.

Sugimoto et al., Female reproduction in mice lacking the prostaglandin F receptor—Roles of prostaglandin and oxytocin receptors in parturition. In Vasopressin and Oxytocin—Molecular, Cellular, and Clinical Advances, Zingg, H. H.; Bourque, C. W.; Bichet, D. G, Eds. Plenum Press Div Plenum Publishing Corp: New York, 1998; vol. 449, pp. 317-321.

Sugimoto et al., Failure of parturition in mice lacking the prostaglandin F receptor. Science 1997, 277, 681-683.

Thormann et al., Conformational properties of azapeptides. Journal of Molecular Structure-Theochem 1999, 469, 63-76.

Vlieghe et al., Synthetic therapeutic peptides: science and market. Drug Discovery Today 2010, 15, 40-56.

\* cited by examiner

| Derivative | MAPK* | Ruffling* |
|---|---|---|
| 10.1 | ↑ | ~ |
| 10.2 | ↑ | ↓ |
| 10.3 | ↓ | ↓ |
| 10.4 | ↓ | ~ |
| 10.0 | ↑ | ↓ |
| PDC | ↑ | ↓ |

*↑: increase in response
↓: decrease in response
~: no effect

FIG. 9

PROSTAGLANDIN-F2 ALPHA RECEPTOR MODULATORS AND USES THEREOF

CROSS REFERENCE TO RELATED APPLICATIONS

This application claims the benefit of U.S. Provisional Patent Application Ser. No. 61/492,540 filed on Jun. 2, 2011, which is incorporated herein by reference in its entirety.

FIELD OF THE INVENTION

The present invention generally relates to prostaglandin-F2 alpha (PGF2α) receptor modulation and uses thereof for the treatment of conditions associated with PGF2α receptor activity such as preterm labor and colorectal cancer.

BACKGROUND OF THE INVENTION

Preterm births (<37 week gestational age) contribute significantly to mortality and morbidity in obstetric practice in developed countries, where rates of preterm delivery vary between 5-13%.[1] In spite of a better understanding of risk factors related to and mechanisms underlying preterm labor, as well as medical interventions to reduce its occurence,[2] the rate of preterm birth has risen in most industrialized countries, increasing in the USA from 9.5% in 1981 to 12.7% in 2005.[3] Preterm birth has major socio-economic implications with associated hospital stays among the most expensive diagnoses for all children:[4] in 2001, preterm birth represented 47% of the costs ($5.8 billion) with all infant hospitalizations and 27% for all pediatric stays. Infant mortality rates are also 15-fold and 75-fold higher for preterm and very preterm (<32 weeks) delivery relative to term births.[4] In addition to morbidity and disability,[5] preterm birth and low birth weight account for many neurodevelopmental disorders,[6] respiratory and gastrointestinal complications,[7] as well as lifelong chronic conditions, such as hypertension and dyslipidemia.[8]

Preterm deliveries are associated with various epidemiological and clinical risk factors; however, >45% are due to spontaneous contraction, for which causes are usually unknown.[1,2] The most effective method for reducing morbidity and mortality related to preterm birth has been early inhibition of the initiation of uterine contractions using labor-suppressing drugs (tocolytics).[9] Tocolytic drugs are used to prolong pregnancy in women with acute risk of preterm birth, caused mainly by active preterm labor and less commonly by ruptured membranes. Classes of medication for tocolysis include β$_2$-adrenergic agonists [Ritodrine® and Terbutaline (Bricanyl®)], calcium channel blockers (i.e., nifedipine), prostaglandin synthetase inhibitors (i.e., indomethacin, Indocid®), an oxytocin antagonist (atosiban (Tractocile®) and magnesium sulfate (FIG. 1).[10-18] In clinical practice, some of these agents have delayed delivery up to 48 h; however, adverse effects have generally limited the utility of most contemporary tocolytics.[10-18] There is thus a need for the development of novel agents and methods for the treatment of preterm labor.

Each year, more than 1 million new cases of colorectal cancer are diagnosed worldwide. In spite of important advances in detection, surgery and chemotherapy, colorectal cancer still represents the second most common cause of cancer death in Canada (Canadian Cancer Society, 2009). The disease is heterologous in nature and characterized by mutations of different effectors like K-Ras and APC and/or the overexpression of inflammatory mediators. Treatment depends on the stage of the cancer and can include surgery, chemotherapy, and radiotherapy. However, these strategies are not effective in all types of patients and are generally associated with serious side effects. There is thus a need for the development of novel agents and methods for the treatment of colorectal cancer.

The present description refers to a number of documents, the content of which is herein incorporated by reference in their entirety.

SUMMARY OF THE INVENTION

The present invention generally relates to prostaglandin-F2 alpha (PGF2α) receptor modulation and uses thereof for the treatment of conditions associated with PGF2α receptor activity such as preterm labor and colorectal cancer.

In a first aspect, the present invention provides a prostaglandin-F2α (PGF2α) receptor (FP) modulator of formula I:

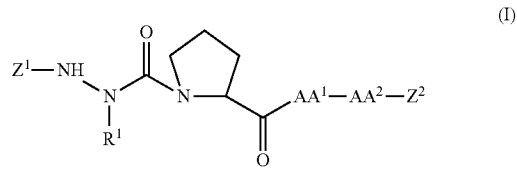

(I)

wherein
$Z^1$ is H or an amino-terminal modifying group;
$R^1$ is H, alkyl, heteroalkyl, aryl, heteroaryl, arylalkyl or heteroarylalkyl, substituted or unsubstituted; saturated or unsaturated; branched or unbranched;
$AA^1$ is a D- or L-amino acid or a surrogate thereof;
$AA^2$ is a D- or L-amino acid or a surrogate thereof;
$Z^2$ is a carboxyl group or a carboxy-terminal modifying group;
or a pharmaceutically acceptable salt thereof.

In an embodiment, $Z^1$ is an acyl group (R—CO—), wherein R is a hydrophobic moiety, or an aroyl group (Ar—CO—), wherein Ar is an aryl group.

In an embodiment, $AA^1$ is Arg, Lys, ornithine, citrulline, pyridylalanine or an arginine surrogate, in a further embodiment pyridylalanine.

In an embodiment, the above-mentioned $AA^2$ is Tyr, Phe, a related alpha-amino acid possessing hydrophobic side chains, an aromatic amine, an aliphatic amine or a primary arylalkylamine, in a further embodiment Phe.

In an embodiment, the above-mentioned carboxy-terminal modifying group is a hydroxamate group, a nitrile group, an amide group, an alcohol or $CH_2OH$.

In an embodiment, $R^1$ is H.

In another embodiment, $R^1$ is an alkyl, in a further embodiment a $C_1$ to $C_6$ alkyl, substituted or unsubstituted; saturated or unsaturated; branched or unbranched. In a further embodiment, $R^1$ is $CH_3$. In another embodiment, $R^1$ is $CH_2CCH$. In another embodiment, $R^1$ is $CH_2CHCH_2$.

In another embodiment, $R^1$ is an arylalkyl, in a further embodiment $CH_2Ph$.

In another aspect, the present invention provides a pharmaceutical composition comprising the above-mentioned FP modulator and a pharmaceutically acceptable excipient.

In another aspect, the present invention provides a method for preventing or treating a disease or condition associated with FP activity, said method comprising administering the above-mentioned FP modulator, or the above-mentioned pharmaceutical composition, to a subject in need thereof.

In another aspect, the present invention provides a use of the above-mentioned FP modulator, or the above-mentioned pharmaceutical composition, for preventing or treating a disease or condition associated with FP activity.

In another aspect, the present invention provides a use of the above-mentioned FP modulator, or the above-mentioned pharmaceutical composition, for the preparation of a medicament for preventing or treating a disease or condition associated with FP activity.

In another aspect, the present invention provides the above-mentioned FP modulator, or the above-mentioned pharmaceutical composition, for the preparation of a medicament for preventing or treating a disease or condition associated with FP activity.

In another aspect, the present invention provides the above-mentioned FP modulator, or the above-mentioned pharmaceutical composition, for preventing or treating a disease or condition associated with FP activity.

In an embodiment, the above-mentioned disease or condition is preterm labor.

In another aspect, the present invention provides a method for determining whether a test compound is an allosteric FP ligand, said method comprising: (a) contacting said test compound with a cell expressing FP in the presence of PGF2α; (b) determining protein kinase C and/or ERK1/2 activity in said cells; and/or (c) determining RhoA/ROCK activity in said cells; wherein (i) an increased protein kinase C and/or ERK1/2 activity and/or (ii) a decreased RhoA/ROCK activity in said cells in the presence of said test compound relative to the absence thereof is indicative that said test compound is an allosteric FP ligand.

In an embodiment, the above-mentioned protein kinase C and/or ERK1/2 activity is determined by measuring the relative amount of phosphorylated protein kinase C and/or ERK1/2 in said cells.

In an embodiment, the above-mentioned RhoA/ROCK activity is determined by measuring the extent of membrane ruffling in said cells.

In another aspect, the present invention provides a method of treating a cancer of the gastrointestinal tract, said method comprising administering to a subject in need thereof a FP modulator.

In another aspect, the present invention provides a use of a FP modulator for treating a cancer of the gastrointestinal tract in a subject.

In another aspect, the present invention provides a use of a FP modulator for the preparation of a medicament for treating a cancer of the gastrointestinal tract in a subject.

In another aspect, the present invention provides an FP modulator for treating a cancer of the gastrointestinal tract in a subject.

In another aspect, the present invention provides an FP modulator for the preparation of a medicament for treating a cancer of the gastrointestinal tract in a subject.

In an embodiment, the FP modulator is the FP modulator of formula I defined above.

In another embodiment, the above-mentioned FP modulator has the following structure:

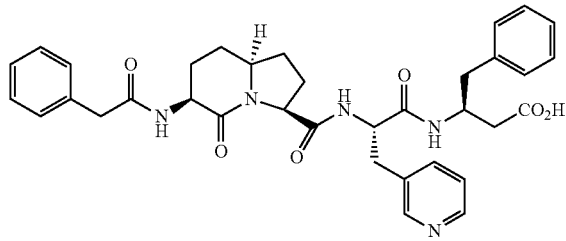 [SMILES: O=C(O)C[C@H](Cc1ccccc1)NC(=O)[C@H](Cc1cccnc1)NC(=O)[C@@H]1CC[C@@H]2CC[C@H](NC(=O)Cc3ccccc3)C(=O)N21]

The present invention also provides novel compounds described herein, including the compounds of formulae I, II, III, Ia, IIa and IIa. The present invention also provides uses of the novel compounds, such as for prostaglandin-F2 alpha (PGF2α) receptor modulation, and for the treatment of conditions associated with PGF2α receptor activity, such as preterm labor and colorectal cancer.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 7A shows the changes in the mean tension (g) expressed as percent of the initial response (% baseline). PDC113.824 or azapeptide (5-9) were given 15 min before PGF2α. Values as mean±SEM of 3-5 experiments for each compound; p<0.05 compared to all values without asterisks. FIG. 7B shows representative traces of contractions for PDC113.824 and azapeptides 7 and 9;

FIG. 9 shows a table summarizing the results with the different compounds on MAPK activation and cell ruffling. 10.0=azapeptide 5, 10.1=azapeptide 6, 10.2=azapeptide 7, 10.3=azapeptide 8, 10.4=azapeptide 9, PDC=PDC113.824;

Figure 11:
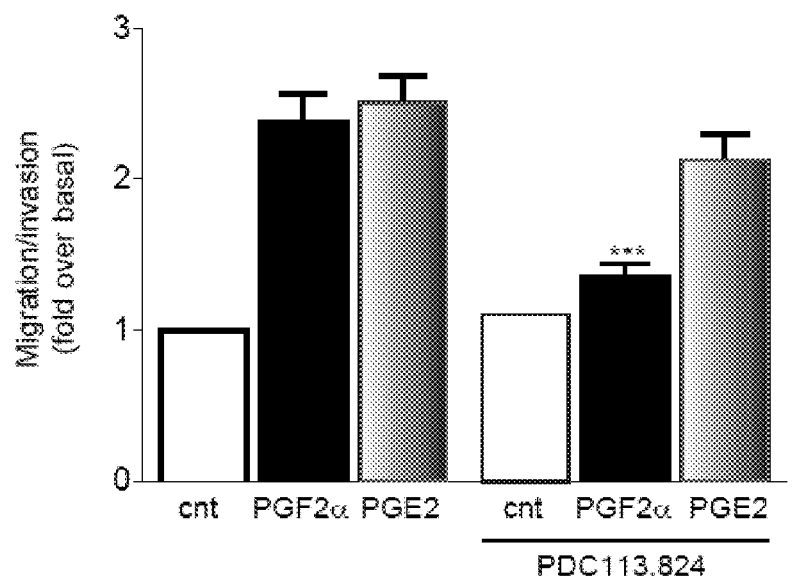
Figure 12:
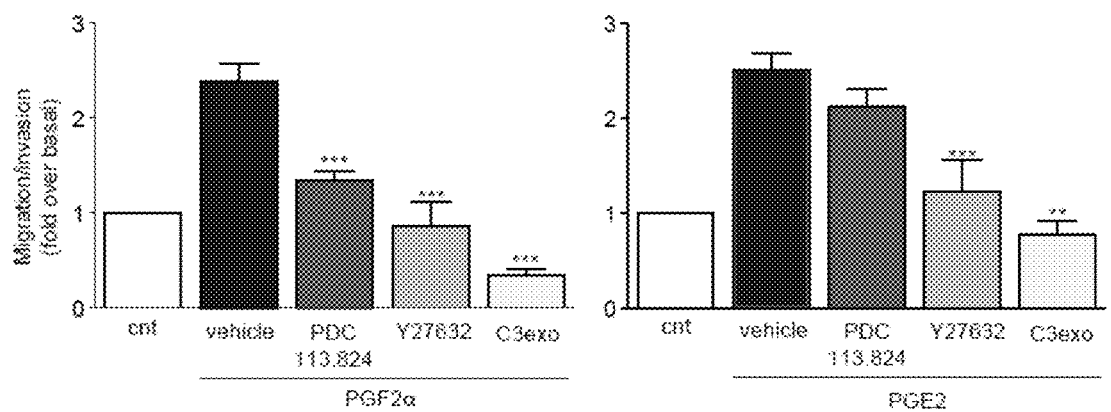
Figure 13:
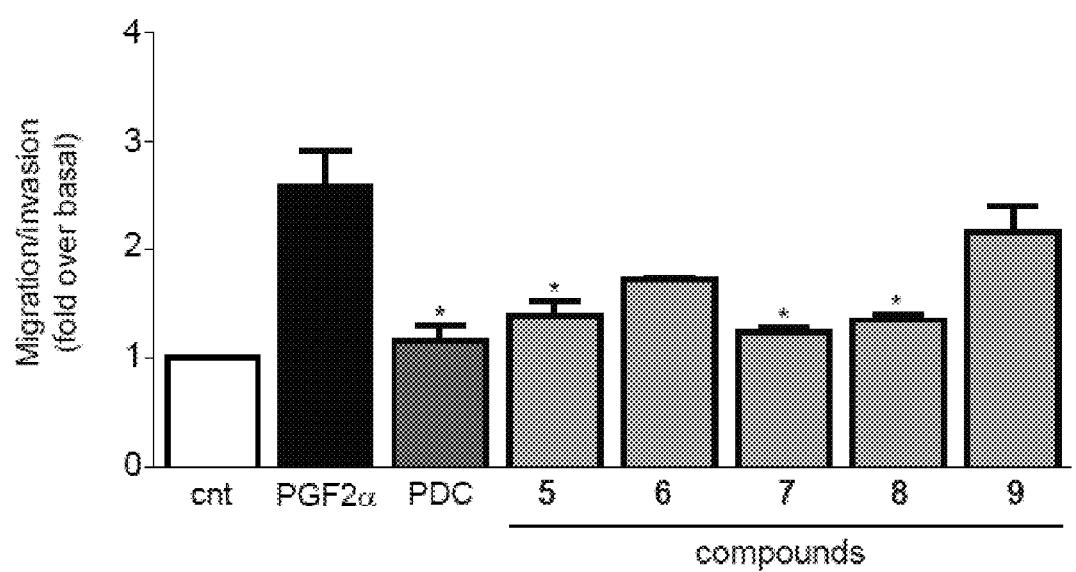

μM) or PGE2 (1 μM). Migration/invation was assessed after 16 h. Results are presented as mean±SEM of 3 independent experiments. *p<0.05, p<0.01, *p<0.001 compared to non-stimulated (ns) conditions;

FIG. 11 shows the effect PDC113.824 on PGF2α- and PGE2-induced migration of colorectal cancer cells. SW480 cells were re-seeded into collagen-coated Boyden chambers, pretreated with PDC (1 μM, 30 min.), and stimulated or not with 1 μM PGF2α and PGE2 (use to show specificity of analogs for FP). Migration/invasion was assessed after 16 h. Results represent mean±SEM of 3 independent experiments. ***p<0.001 compared to control (cnt);

FIG. 12 shows that PGF2α- and PGE2-dependent migration of colorectal cancer cells is mediated by the RhoA/ROCK signaling pathway. SW480 cells were re-seeded into collagen-coated Boyden chambers, pretreated with PDC113.824 (1 μM, 30 min.), the RhoA/ROCK inhibitors Y27632 (25 μM, 30 min.) or C3 exoenzyme (C3exo, 10 μg/ml, 4 h), and stimulated or not with 1 μM PGF2α or PGE2. Migration/invasion was assessed after 16 h. Results represent mean±SEM of 3 independent experiments. p<0.01, p<0.001 compared to control (cnt); and FIG. 13 shows the effects of azapeptides 5-9 on PGF2α-dependent migration of colorectal cancer cells. SW480 cells were re-seeded into collagen-coated Boyden chambers, pretreated with PDC113.824 or azapeptides 5-9 (1 μM, 30 min.), and stimulated or not with 1 μM PGF2α. Migration/invasion was assessed after 16 h. Results represent mean±SEM of 3 independent experiments. *p<0.05 compared to control (cnt).

DESCRIPTION OF ILLUSTRATIVE EMBODIMENTS

In the studies described herein, the present inventors have synthesized novel azapeptides having allosteric FP modulatory activity. These azapeptides are easy to synthesize, and their method of synthesis is more readily amenable to analog preparation by application of the submonomer approach for azapeptide synthesis, as described in more detail below. They show that these azapeptides reduce the magnitude or duration of PGF2α-induced myometrial contractions. They also demonstrate that PGF2α receptor modulators inhibit the migration of colorectal cancer cells.

Accordingly, in an aspect, the present invention provides a FP modulator of formula I:

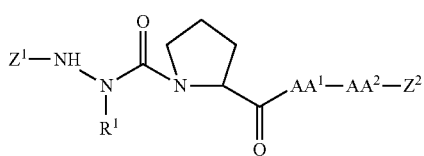
(I)

wherein $Z^1$ is H or an amino-terminal modifying group, in an embodiment a straight chained or branched alkyl group of one to eight carbons, or an acyl group (R—CO—), wherein R is a hydrophobic moiety (e.g., acetyl, propionyl, butanyl, iso-propionyl, or iso-butanyl), or an aroyl group (Ar—CO—), wherein Ar is an aryl group. In an embodiment, the acyl group is a $C_1$-$C_{16}$ or $C_3$-$C_{16}$ acyl group (linear or branched, saturated or unsaturated), in a further embodiment, a saturated $C_1$-$C_6$ acyl group (linear or branched) or an unsaturated $C_3$-$C_6$ acyl group (linear or branched), for example an acetyl group ($CH_3$—CO—, Ac);

wherein $R^1$ is H, alkyl (linear or cycloalkyl), heteroalkyl, aryl, heteroaryl, arylalkyl or heteroarylalkyl (substituted or unsubstituted; saturated or unsaturated; branched or unbranched); Z is a carboxyl group or a carboxy-terminal modifying group (e.g., attached via an ester linkage), in an embodiment, a hydroxamate group, a nitrile group, an amide (primary, secondary or tertiary amide) group, an alcohol or $CH_2OH$; or a pharmaceutically acceptable salt thereof.

In an embodiment, the substituted or unsubstituted alkyl (linear or cycloalkyl), heteroalkyl, aryl, heteroaryl, arylalkyl or heteroarylalkyl is branched. In an embodiment, the branched alkyl, heteroalkyl, aryl, heteroaryl, arylalkyl or heteroarylalkyl has one or two branches, in a further embodiment one branch.

In an embodiment, the substituted alkyl (linear or cycloalkyl), heteroalkyl, aryl, heteroaryl, arylalkyl or heteroarylalkyl is mono-, di- or tri-substituted. In an embodiment, the substituent is a halogen, a haloalkyl, a hydroxy, an aryl, a heterocyclyl or a heteroaryl.

In an embodiment, $R^1$ is an unsubstituted alkyl, heteroalkyl, aryl, heteroaryl, arylalkyl or heteroarylalkyl.

In another embodiment, $R^1$ is an unbranched alkyl, heteroalkyl, aryl, heteroaryl, arylalkyl or heteroarylalkyl.

In another embodiment, $R^1$ is an unsaturated alkyl, heteroalkyl, aryl, heteroaryl, arylalkyl or heteroarylalkyl, for example an alkenyl, alkynyl, heteroalkenyl, heteroalkynyl, arylalkenyl, arylalkynyl, heteroarylalkenyl or heteroarylalkynyl. In an embodiment, the unsaturated alkyl has at least one double bond and/or at least one triple bond. In an embodiment, the unsaturated alkyl has one double bond. In an embodiment, the unsaturated alkyl has one triple bond.

In an embodiment, $R^1$ has from 1 to 18 carbon atoms. In further embodiments from $R^1$ is an alkyl (saturated, alkenyl, alkynyl) having from 1 to 12 (2 to 12 for alkenyl, alkynyl), 1 to 8 (2 to 8 for alkenyl, alkynyl), 1 to 6 (2 to 6 for alkenyl, alkynyl), 1 to 4 (2 to 4 for alkenyl, alkynyl) or 1 to 3 (2 or 3 for alkenyl, alkynyl) carbon atoms.

In a further embodiment, $R^1$ is H, $CH_3$, $CH_2CCH$, $CH_2Ph$ or $CH_2CHCH_2$. In an embodiment, $R^1$ is H. In another embodiment, $R^1$ is $CH_3$. In another embodiment, $R^1$ is $CH_2CCH$. In another embodiment, $R^1$ is $CH_2Ph$. In another embodiment, $R^1$ is $CH_2CHCH_2$.

$AA^1$ is an amino acid (D- or L-) or a surrogate thereof, for example a basic amino acid or a surrogate thereof, in an embodiment Arg, Lys, ornithine, citrulline, pyridylalanine (2-, 3- or 4-pyridylalanine) or an arginine surrogate (e.g., 4-amidinophenylacetyl, 4-amidinophenylpropionyl, 4-amidinophenylglycyl, 4-amidinophenylmethylglycyl, 4-guanidinophenylacetyl, 4-guanidinophenylpropionyl, 4-guanidinophenylglycyl, and 4-guanidinophenylmethylglycyl), in a further embodiment pyridylalanine. In an embodiment, $AA^1$ is a D-amino acid or a surrogate thereof. In an embodiment, $AA^1$ is an L-amino acid or a surrogate thereof.

$AA^2$ is an amino acid (D- or L-) or a surrogate thereof, for example an aromatic amino acid or a surrogate thereof, in an embodiment Tyr, Phe, a related alpha-amino acid possessing hydrophobic side chains, an aromatic amine, an aliphatic amine or a primary arylalkylamine, in a further embodiment Phe.

$Z^2$ is a carboxyl group (i.e., the native carboxy terminal of the peptide), or a carboxy-terminal modifying group (e.g., attached via an ester linkage), in an embodiment, an hydroxamate group, a nitrile group, an amide (primary, secondary or tertiary) group, an aliphatic amine of one to ten carbons such as methyl amine, iso-butylamine, iso-valerylamine or cyclohexylamine, an aromatic or arylalkyl amine such as aniline, napthylamine, benzylamine, cinnamylamine, or phenylethylamine, an alcohol or $CH_2OH$.

In an embodiment, the above-noted acyl group of $Z^1$ is benzoyl, acetyl, tert-butyl acetyl, para-phenyl benzoyl, trifluoroacetyl, cyclohexylcarbonyl or phenylacetyl.

In an embodiment, the above-noted hydrophobic moiety is a substituted or unsubstituted alkyl, a substituted or unsubstituted cycloalkyl, a phenylmethyl, or a saturated or unsaturated hydrocarbon chain.

In an embodiment, $Z^1$ is

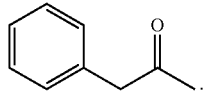

In an embodiment, $Z^2$ is a carboxyl group.

In another aspect, the present invention provides a FP modulator of formula II:

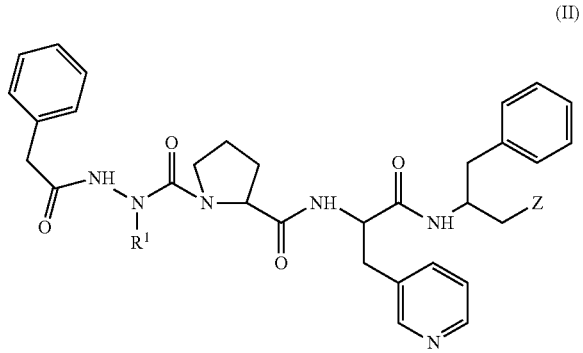

(II)

wherein $R^1$ is s defined above and Z corresponds to the definition of $Z^2$ above.

In another aspect, the present invention provides a FP modulator of formula III:

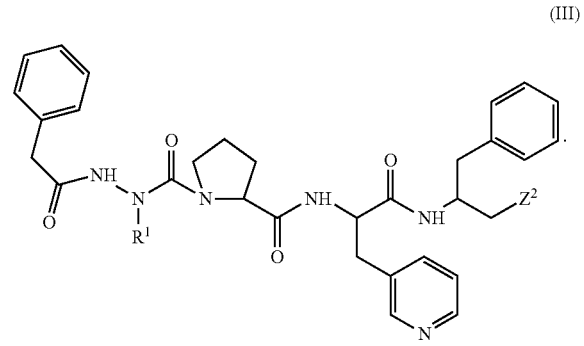

(III)

wherein $R^1$ and $Z^2$ are as defined above;
or a pharmaceutically acceptable salt thereof.

In an embodiment, the above-mentioned FP modulator inhibits PGF2α-mediated activation of the Rho/ROCK signaling pathways in a cell (e.g., a human myometrial cell). In an embodiment, the above-mentioned FP modulator inhibits actin remodeling and/or contraction of a cell (e.g., a human myometrial cell). In an embodiment, the above-mentioned FP modulator stimulates or increases PGF2α-mediated protein kinase C, MAPK and/or ERK1/2 signaling in a cell (e.g., a human myometrial cell). In an embodiment, the above-mentioned FP modulator increases FP receptor coupling to $Gα_q$. In an embodiment, the above-mentioned FP modulator decreases FP receptor coupling to $Gα_{12}$.

As used herein, the term "arylalkyl" means an alkyl group (e.g., a lower alkyl group) where one of the hydrogens is substituted with aryl (e.g., benzene, naphthalene, anthracene, or phenanthrene). Exemplary arylalkyl groups include benzyl and phenethyl. Arylalkyl groups may be unsubstituted or substituted with, for example, 1, 2, 3, 4, 5, 6, or 7 substituent groups located at any position (i.e., on the $sp^2$ or the $sp^3$ hybridized carbons of the group).

As used herein, the term "aryl" means mono- or bicyclic carbocyclic ring system having 6 to ten carbon atoms form one or two aromatic rings and is exemplified by phenyl, naphthyl, 1,2-dihydronaphthyl, 1,2,3,4-tetrahydronaphthyl, fluorenyl, indanyl, indenyl, tolyl, alkyloxyphenyl, alkyloxycarbonylphenyl, halophenyl and the like, and may be optionally substituted with one, two, three, four, five or six substituents located at any position of the ring.

As used herein, the term "heteroarylalkyl" means an alkyl group (e.g., a lower alkyl group) where one of the hydrogens is substituted with heteroaryl. Heteroarylalkyl groups may be unsubstituted or substituted with, for example, 1, 2, 3, 4, 5, 6, or 7 substituent groups.

The term "heteroaryl," as used herein, represents that subset of heterocycles, as defined herein, which are aromatic: i.e., they contain 4n+2 pi electrons within the mono- or multicyclic ring system. Illustrative examples of heteroaryl groups include, but are not limited to, pyridyl, pyridazinyl, pyrazinyl, pyrimidinyl, triazinyl, quinolinyl, isoquinolinyl, quinoxalinyl, quinazolinyl, benzotriazinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, imidazopyridines, benzothiaxolyl, benzofuranyl, benzothienyl, indolyl, isothiazolyl, pyrazolyl, indazolyl, imidazolyl, triazolyl, tetrazolyl, oxazolyl, isoxazolyl, oxadiazolyl, thiadiazolyl, pyrrolyl, thiazolyl, furyl, thienyl and the like. Five- or six-membered monocyclic heteroaryl rings include: pyridyl, pyridazinyl, pyrazinyl, pyrimidinyl, triazinyl, isothiazolyl, pyrazolyl, imidazolyl, triazolyl, tetrazolyl, oxazolyl, isoxazolyl, oxadiazolyl, thiadiazolyl, pyrrolyl, thiazolyl, furyl, thienyl and the like. Eight- to ten-membered bicyclic heteroaryl rings having one to four heteroatoms include: quinolinyl, isoquinolinyl, quinoxalinyl, quinazolinyl, benzotriazinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, imidazopyridinyl, benzothiaxolyl, benzofuranyl, benzothienyl, indolyl, indazolyl, and the like. Heteroaryls may be unsubstituted or substituted with 1, 2, 3, 4, 5, or 6 substituents.

The terms "alkyl" as used herein, are inclusive of both straight chain and branched chain saturated groups of from 1 to 18 carbons, unless otherwise specified. The term "lower alkyl" as used herein means alkyl groups of from 1 to 7 carbon atoms that consist of a straight, branched or cyclic configuration. Lower alkyls may include 1, 2, 3, 4, 5, 6, or 7 carbon atoms. Examples of lower alkyl groups include, but are not limited to: methyl, ethyl, propyl, isopropyl, n-, sec-, iso- and ter-butyl, pentyl, isoamyl, hexyl, heptyl, cyclopropyl, cyclobutyl, cyclopentyl, cyclohexyl, cyclobutylmethyl, and cycloheptyl, among others. A lower alkyl may be optionally substituted.

The term "heteroalkyl" refers to an alkyl as described above in which at least one carbon of the alkyl is replaced by a heteroatom, for example N, O, P, B, S, Si, Sb, Al, Sn, As, Se or Ge.

The term "alkenyl" as used herein, represents monovalent straight or branched chain groups of, unless otherwise specified, from 2 to 7 carbons containing one or more carbon-carbon double bonds. The radical may be a linear or branched chain, in the E or Z form, and optionally substituted with one to three substituents. Illustrative examples of alkenyl groups include, but are not limited to, vinyl, 1-propenyl, 2-propenyl, isopropenyl, 1-butenyl, 2-butenyl, isobutenyl, 2-methyl-1-propenyl, 1-pentenyl, 2-pentenyl, 4-methyl-2-pentenyl, 1,3-pentadienyl, 2,4-pentadienyl, 1,3-butadienyl and the like.

As used herein, the term "alkynyl" means monovalent, unbranched or branched hydrocarbon chain having one or more triple bonds therein. The triple bond of an alkynyl group can be unconjugated or conjugated to another unsaturated group. Suitable alkynyl groups include, but are not limited to, $(C_2-C_6)$ alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or optionally substituted with one or two suitable substituents.

Where a group may be optionally substituted, optional substituents include, but are not limited to: hydroxy (—OH), —CN, —NO₂, halogen (i.e., —F, —Cl, —Br, or —I), —CO₂H, —CO₂(lower alkyl), —CO₂(lower alkoxyalkyl), -(lower alkyl), -(lower alkoxyalkyl), —O(lower alkyl), —O(lower alkoxyalkyl), —NH(lower alkyl), —NH(lower alkoxyalkyl), —N(lower alkyl)₂, and —N(lower alkoxyalkyl)₂. In some embodiments, a substituted group may have 1, 2, 3, 4, 5, 6, 7, 8, or 9 substituents located at any position. In some embodiments, a substituent group that includes lower alkyl or lower alkoxy is further substituted.

As used herein, "amino acid" refers to a compound comprising an amino functional group and a carboxylic functional group. Types of amino acids include "α-amino acids," wherein the amino and carboxylic groups are attached to the same carbon. In "β-amino acids" the carbon to which the amino group is attached is adjacent to the carbon to which the carboxylic group is attached, and in "γ-amino acids," there is an additional intervening carbon. Amino acids can have the L-configuration (for example, natural amino acids have the L-configuration) or the D-configuration. Amino acids include natural amino acids and unnatural amino acids. A "natural amino acid" refers to an amino acid that is naturally produced or found in a mammal. Natural amino acids can be encoded by the standard genetic code or may result from, for example, post-translational modifications. Natural amino acids include the twenty proteinogenic L-amino acids (Alanine (A), Cysteine (C), Serine (S), Threonine (T), Aspartic Acid (D), Glutamic Acid (E), Asparagine (N), Glutamine (Q), Histidine (H), Arginine (R), Lysine (K), Isoleucine (I), Leucine (L), Methionine (M), Valine (V), Phenylalanine (F), Tyrosine (Y), Tryptophan (W), Glycine (G), and Proline (P)). Preferred natural amino acids for use in any of the compositions and methods of the invention include L-phenylalanine and L-proline. An "unnatural amino acid" is an amino acid that is not naturally produced (e.g., encoded by the genetic code or resulting from a posttranslational modification) or naturally found in a mammal. Unnatural amino acids include amino acids that normally do not occur in proteins (e.g., an α-amino acid having the D-configuration, or a (D,L)-isomeric mixture thereof), homologues of naturally occurring amino acids, an α,α-disubstituted analogue of a naturally occurring amino acid, or an α-amino acid wherein the amino acid side chain has been shortened by one or two methylene groups or lengthened to up to 10 carbon atoms.

Other amino acids include for example non-genetically encoded forms of amino acids, as well as a conservative substitution of an L-amino acid. Naturally-occurring non-genetically encoded amino acids include, for example, beta-alanine, 3-amino-propionic acid, 2,3-diamino propionic acid, alpha-aminoisobutyric acid (Aib), 4-amino-butyric acid, N-methylglycine (sarcosine), hydroxyproline, ornithine (e.g., L-ornithine), citrulline, t-butylalanine, t-butylglycine, N-methylisoleucine, phenylglycine, cyclohexylalanine, norleucine (Nle), norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine, sulfoxide, L-homoarginine (Hoarg), N-acetyl lysine, 2-amino butyric acid, 2-amino butyric acid, 2,4,-diaminobutyric acid (D- or L-), p-aminophenylalanine, N-methylvaline, homocysteine, homoserine (HoSer), cysteic acid, epsilon-amino hexanoic acid, delta-amino valenric acid, or 2,3-diaminobutyric acid (D- or L-), etc. These amino acids are well known in the art of biochemistry/peptide chemistry.

The term "pharmaceutically acceptable salt," as used herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, S. M. Berge et al. describe pharmaceutically acceptable salts in detail in *J Pharmaceutical Sciences* 66: 1-19, 1977. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The present invention includes all tautomers and stereoisomers of compounds of Formulas I to III, either in admixture or in pure or substantially pure form. The compounds of the present invention can have asymmetric centers at the carbon atoms, and therefore the compounds of Formulas I to III can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

In an embodiment, the FP modulator is a compound of formula Ia:

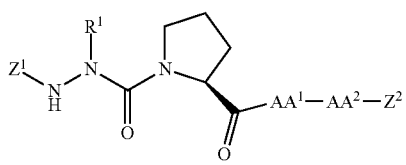

wherein $Z^1$, $R^1$, $AA^1$, $AA^2$ and $Z^2$ are as defined above.

In an embodiment, the FP modulator is a compound of formula IIa:

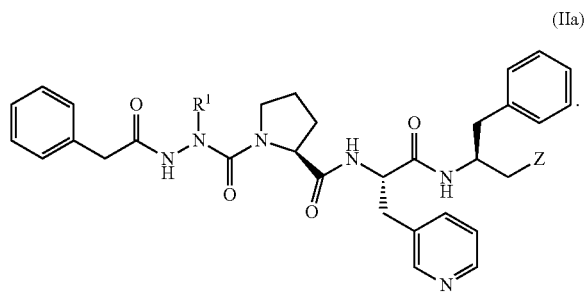

wherein $R^1$ and Z are as defined above.

In an embodiment, the FP modulator is a compound of formula IIIa:

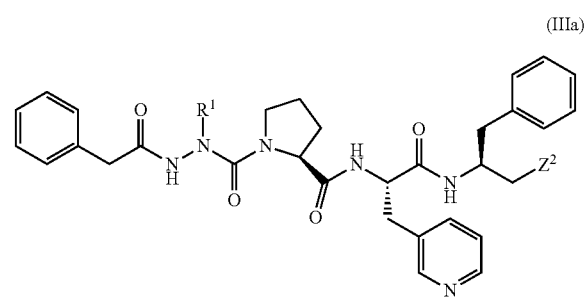

wherein $R^1$ and $Z^2$ are as defined above.

The FP modulators of the present invention may further comprise modifications that confer additional biological properties to the FP modulators such as protease resistance, plasma protein binding, increased plasma half-life, intracellular penetration, etc. Such modifications include, for example, covalent attachment of fatty acids (e.g., $C_6$-$C_{18}$) to the FP modulators, attachment to proteins such as albumin; glycosylation, biotinylation or PEGylation. The above description of modification of the FP modulators does not limit the scope of the approaches nor the possible modifications that can be engineered.

In an embodiment, the above-mentioned FP modulator is substantially pure. A compound is "substantially pure" when it is separated from the components that naturally accompany it. Typically, a compound is substantially pure when it is at least 60%, more generally 75%, 80% or 85%, preferably over 90% and more preferably over 95% (96, 97, 98 or 99%), by weight, of the total material in a sample. Purity can be measured using any appropriate method such as column chromatography, gel electrophoresis, HPLC, etc.

Figure 5:
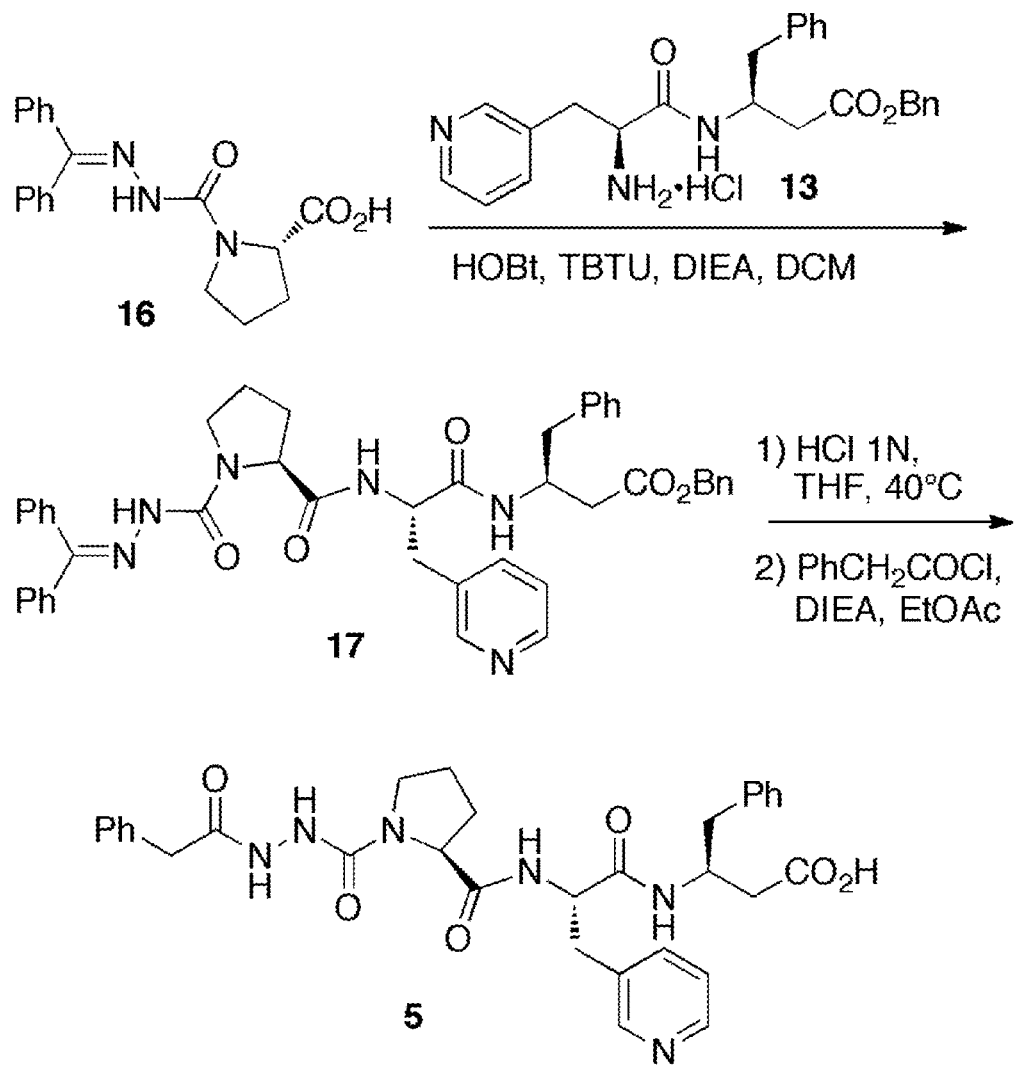
FIG. 5 shows steps in the synthesis of AzaGly-Pro mimic 5 (Scheme 3)
Figure 6:
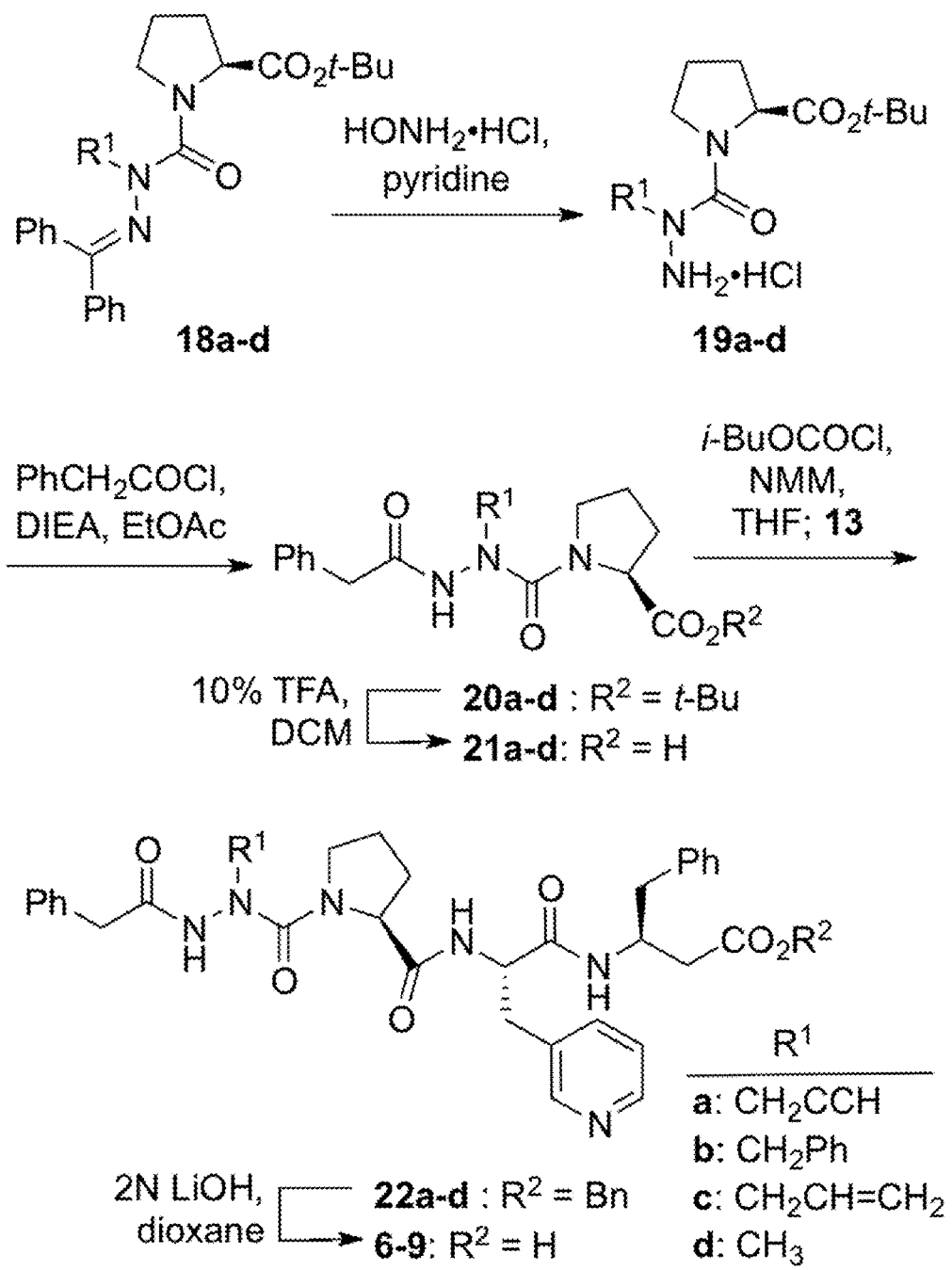
FIG. 6 shows steps in the synthesis of AzaGly-Pro mimics 6-9 (Scheme 4)

The azapeptide-based FP modulators described herein may be synthesized, for example, using the method described in Example 1 below (FIGS. 5 and 6).

In another aspect, the present invention provides a pharmaceutical composition comprising the above-mentioned FP modulator and one or more pharmaceutically acceptable carriers, diluents and/or excipients. Such compositions may be prepared in a manner well known in pharmaceutical art. Supplementary active compounds can also be incorporated into the compositions. As used herein "pharmaceutically acceptable carrier", "diluent" or "excipient" includes any and all solvents, buffers, dispersion media, coatings, antibacterial and antifungal agents, isotonic and absorption delaying agents, and the like that are physiologically compatible. The carrier can be suitable, for example, for intravenous, parenteral, subcutaneous, intramuscular, intracranial, intraorbital, ophthalmic, intraventricular, intracapsular, intraspinal, intrathecal, epidural, intracisternal, intraperitoneal, intranasal, intrauterine, intramyometrial or pulmonary (e.g., aerosol) administration (see Remington: The Science and Practice of Pharmacy by Alfonso R. Gennaro, 2003, 21th edition, Mack Publishing Company).

In another aspect, the present invention provides a method of preventing or treating a condition/disease associated with PGF2α and/or FP activity, the method comprising administering an effective amount of the above-mentioned FP modulator of formulas I-III and Ia-IIIa to a subject in need thereof. In an embodiment, the above-mentioned disease or condition is preterm/premature labor (i.e., to arrest uterine contractions associated with labor with a view to prolong gestation), dysmenorrhea/menstrual cramps (i.e., to arrest uterine spasms associated with dysmenorrhea), or cancer of the gastrointestinal tract (e.g., colorectal cancer). In an embodiment, the condition is preterm/premature labor and R is H, $CH_2CCH$, $CH_2Ph$ or $CH_3$, in a further embodiment R is H, $CH_2CCH$ or $CH_2Ph$. In an embodiment, the above-mentioned FP modulator is administered by an intrauterine or intramyometrial route.

In another aspect, the present invention provides a method of treating a cancer of the gastrointestinal tract (e.g., colorectal cancer), the method comprising administering an effective amount of FP modulators to a subject in need thereof. FP modulators are known in the art and include, for example, those described in PCT publication no. WO/2003/104266 (incorporated herein by reference).

Examples of FP modulators include the following peptides disclosed in PCT publication no. WO/2003/104266 (Table 1):

| Compound No | Peptide name | Sequence (N to C) |
|---|---|---|
| 1 | THG113 | i l g h r d y k |
| 2 | THG113.1 | g h r d y k |
| 3 | THG113.2 | i l g a r d y k |
| 4 | THG113.3 | i l g h a d y k |
| 5 | THG113.4 | i l g h r a y k |
| 6 | THG113.5 | i l g H r a y k |

-continued

| Compound No | Peptide name | Sequence (N to C) |
|---|---|---|
| 7 | THG113.6 | i l g h R d e k |
| 8 | THG113.7 | i l g h r D y k |
| 9 | THG113.8 | i l a h r d y k |
| 10 | THG113.9 | i l A h r d y k |
| 11 | THG113.10 | i l g h r d y w |
| 12 | THG113.11 | i l g h r d e k |
| 13 | THG113.12 | i l g f r d y k |
| 14 | THG113.13 | i l g h r e y k |
| 15 | THG113.14 | i l g h k d y k |
| 16 | THG113.15 | i l g h r n y k |
| 17 | THG113.16 | i l g h r d y |
| 18 | THG113.17 | i l p h r d y k |
| 19 | THG113.18 | i l h r d y k |
| 20 | THG113.19 | i l g h q d y k |
| 21 | THG113.20 | i l g h r s y k |

-continued

| Compound No | Peptide name | Sequence (N to C) |
|---|---|---|
| 22 | THG113.21 | i l g h r d y-amide |
| 23 | THG113.22 | i l g h r d y k-amide |
| 24 | THG113.23 | i l g w r d y k |
| 25 | THG113.24 | i l g y r d y k |
| 26 | THG113.25 | i l g-(cha)-r d y k |
| 27 | THG113.26 | i l g (cha) q d y k |
| 28 | THG113.27 | i l g (cha) r n y k |
| 29 | THG113.28 | k y d r h g l l |
| 30 | THG113.29 | i l g h-(3PA)-q d y k |
| 31 | THG113.30 | i l g h-(4PA)-d y k |
| 32 | THG113.31 | i l g h (cit) d y k |

Small letters: D-amino acids; capital letters: L-amino acids; cha: D-cyclohexylalanine; PA: L-pyridylalanlne; cit: D-citrulline.

In an embodiment, the FP modulator is a peptide comprising, or consisting of, the sequence ilgh(cit)dyk (all D amino-acids; cit=D-citruline, peptide 32 in the Table above).

Examples of FP modulators include the following peptidomimetics disclosed in PCT publication no. WO/2003/104266 (Table 2):

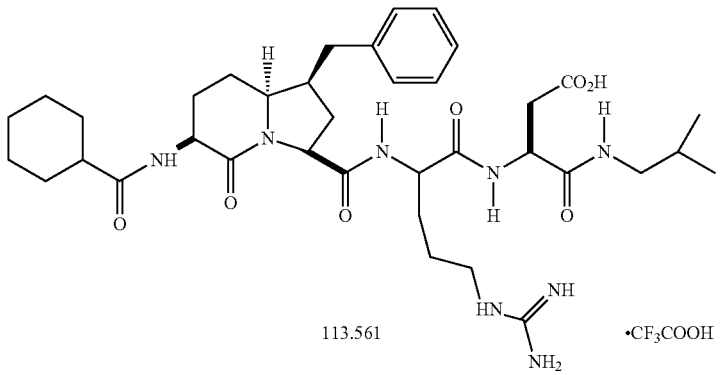

113.561 •CF₃COOH

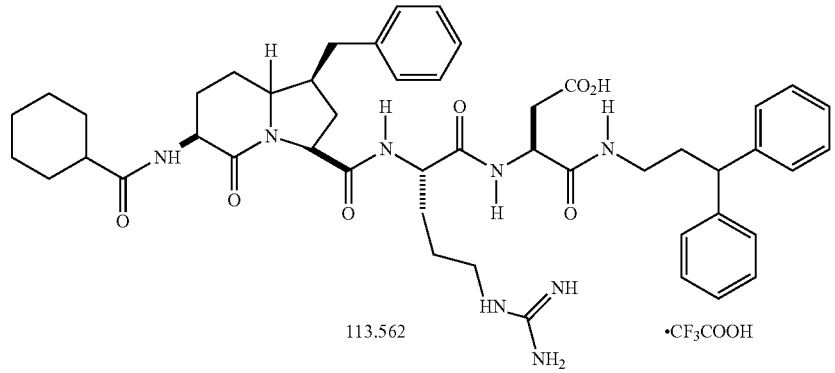

113.562 •CF₃COOH

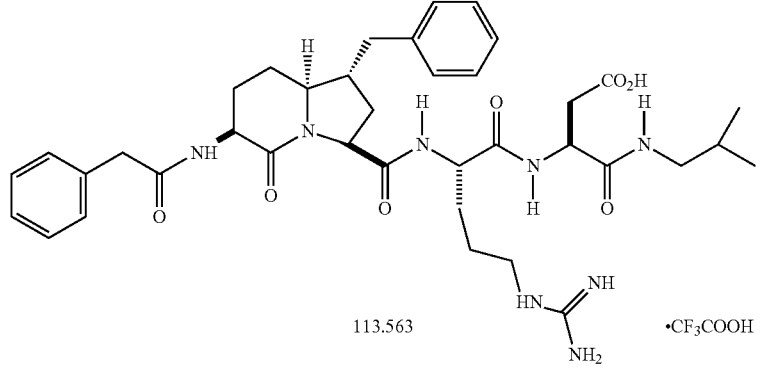
35
113.563 •CF₃COOH
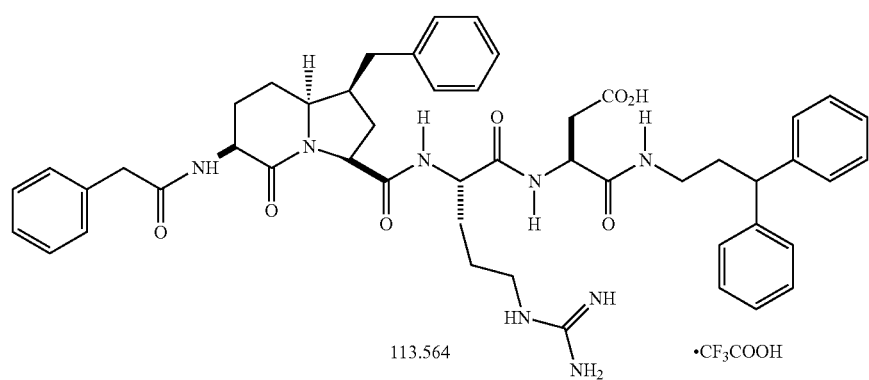
36
113.564 •CF₃COOH
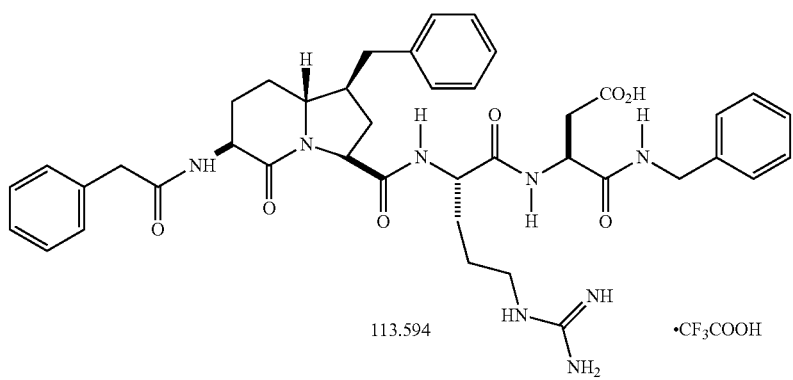
37
113.594 •CF₃COOH
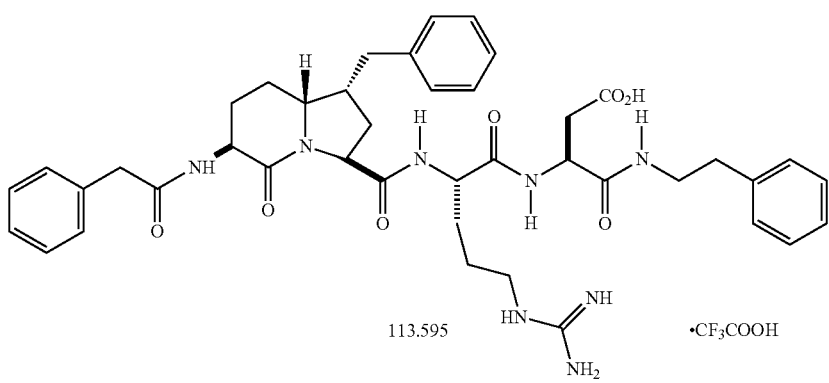
38
113.595 •CF₃COOH -continued
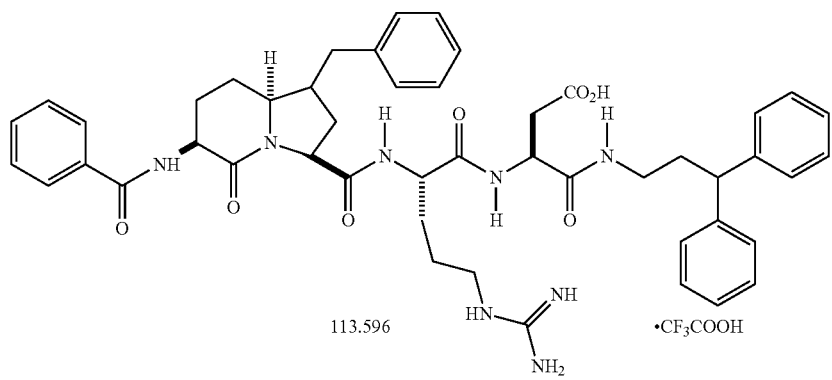
39
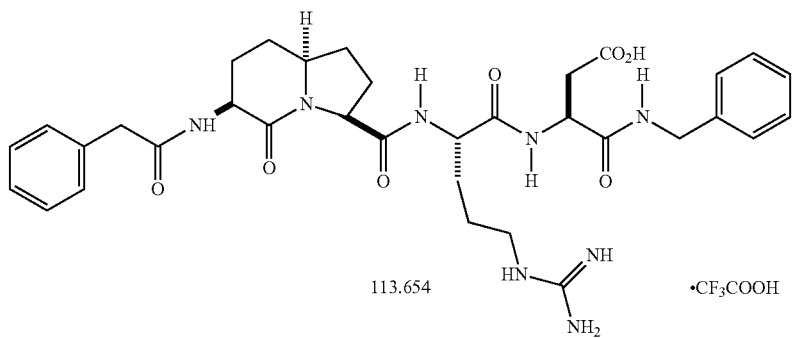
40
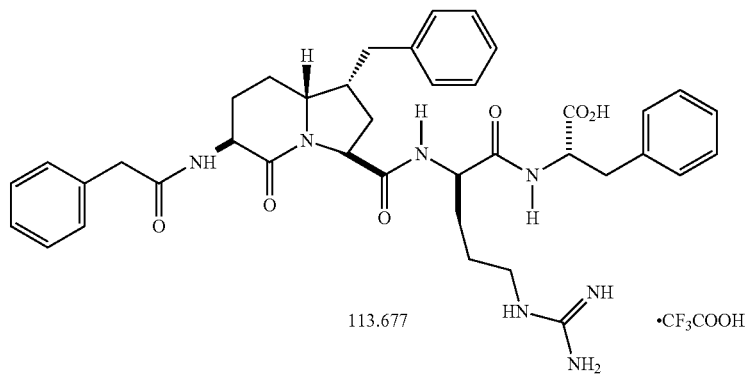
41
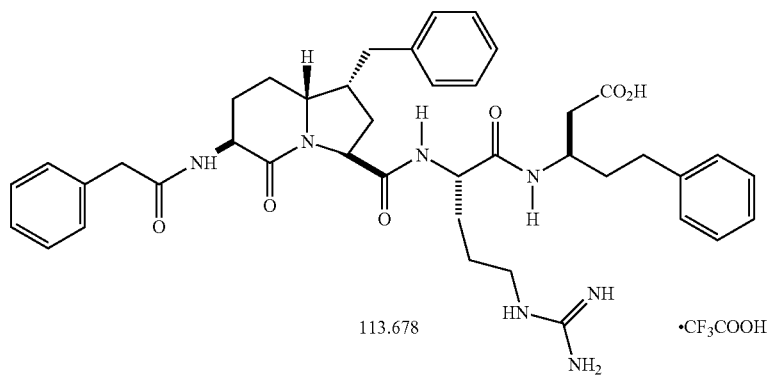
42

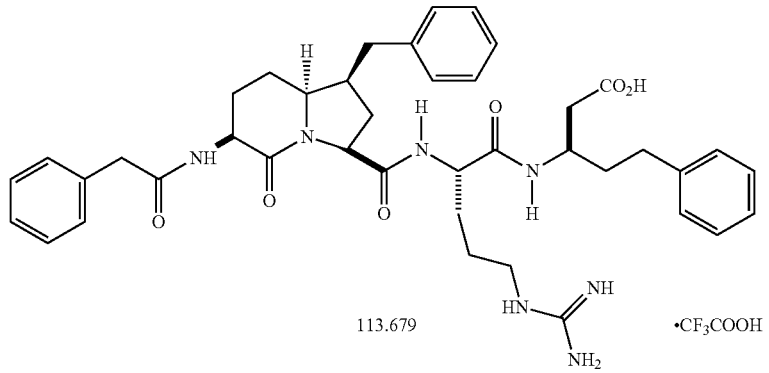
43
113.679 •CF₃COOH
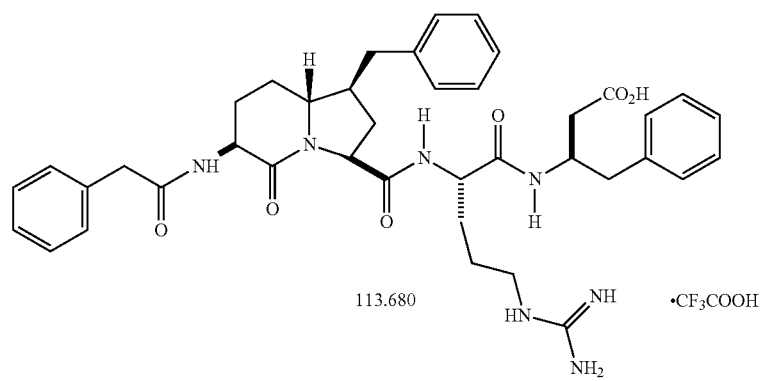
44
113.680 •CF₃COOH
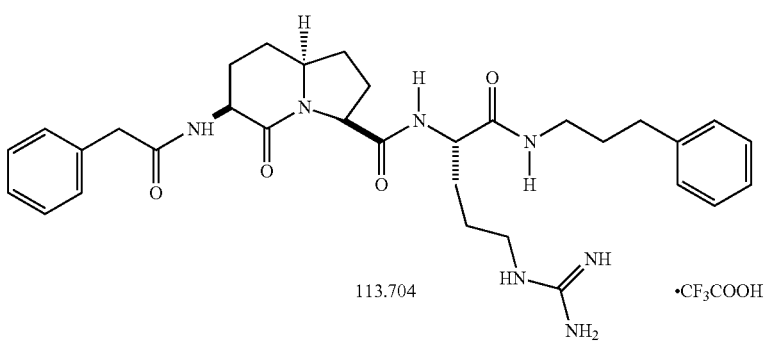
45
113.704 •CF₃COOH
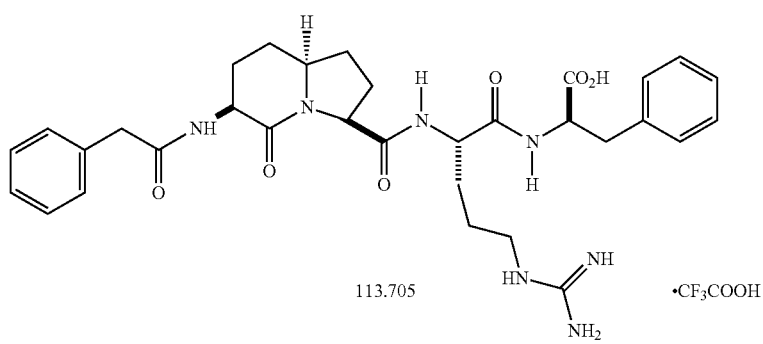
46
113.705 •CF₃COOH

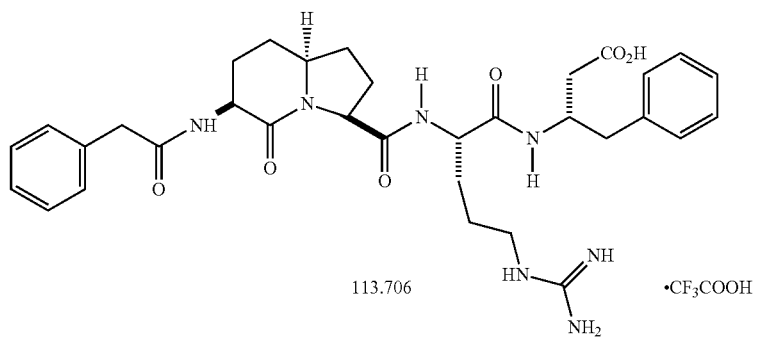
47
113.706 •CF₃COOH
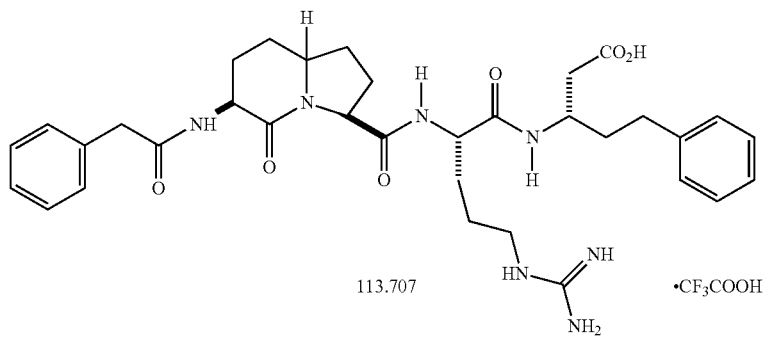
48
113.707 •CF₃COOH
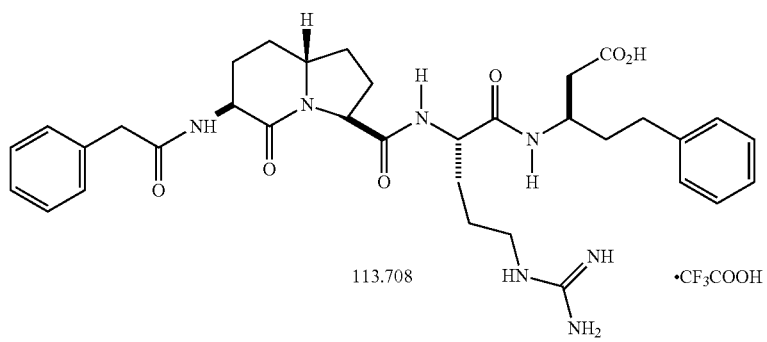
49
113.708 •CF₃COOH
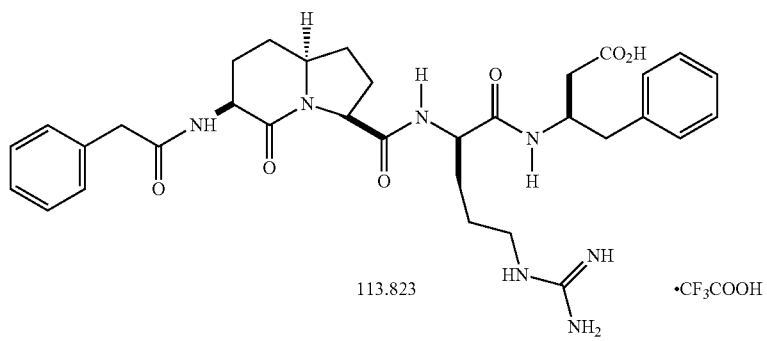
50
113.823 •CF₃COOH

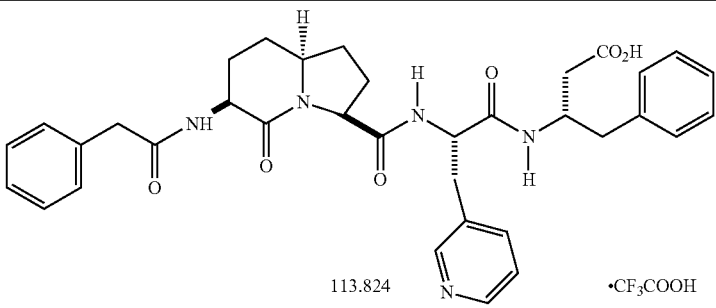

113.824  •CF₃COOH  51

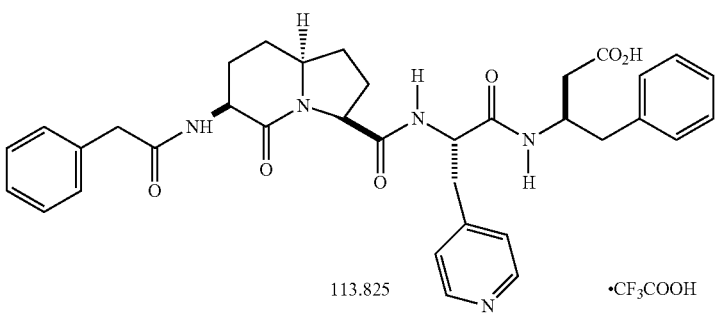

113.825  •CF₃COOH  52

In an embodiment, the above-mentioned FP modulator is an allosteric modulator. In an embodiment, the FP modulator has the following structure (PDC113.824, compound 51 in the table above):

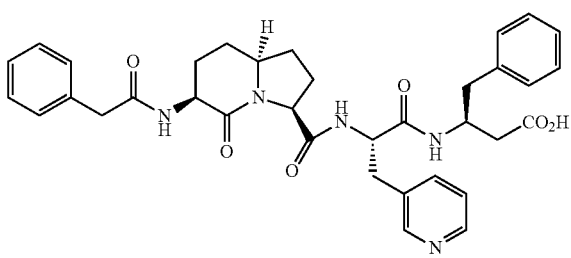 [SMILES: O=C(O)C[C@H](Cc1ccccc1)NC(=O)[C@H](Cc1cccnc1)NC(=O)[C@@H]1CC[C@@H]2CC[C@H](NC(=O)Cc3ccccc3)C(=O)N21]

In another embodiment, the FP modulator is a FP modulator of formulas I-III and Ia-IIIa defined above. In a further embodiment, the FP modulator is a PGF2α receptor modulator of formulas I-III and Ia-IIIa defined above in which $R^1$ is H, $CH_2CCH$, $CH_2Ph$ or $CH_2CH=CH_2$, in a further embodiment H, $CH_2Ph$ or $CH_2CH=CH_2$.

In another aspect, the present invention provides a method (e.g., an in vitro method) for determining whether a test compound may be useful for the treatment of a cancer of the gastrointestinal tract (e.g., colorectal cancer), the method comprising contacting a cell expressing FP with the test compound; and determining whether said test compound inhibit the activity and/or expression of FP, wherein said inhibition is indicative that the test compound may be useful for the treatment of a cancer of the gastrointestinal tract. In an embodiment, the above-mentioned contacting is performed in the presence of FP agonists (e.g., PGF2α). In an embodiment, the method further comprises determining MAP kinase activity in said cell; and/or (c) determining RhoA/ROCK activity in said cell; wherein (i) an increased MAP kinase activity and/or (ii) a decrease RhoA/ROCK activity in said cell in the presence of said test compound relative to the absence thereof is indicative that said test compound is an allosteric FP modulator and may be useful for the treatment of a cancer of the gastrointestinal tract (e.g., colorectal cancer).

In another aspect, the present invention provides a method (e.g., an in vitro method) for determining whether a test compound may be useful for the treatment of a cancer of the gastrointestinal tract (e.g., colorectal cancer), the method comprising contacting FP with the test compound; and determining whether said test compound binds FP, wherein said binding is indicative that the test compound may be useful for the treatment of a cancer of the gastrointestinal tract. In an embodiment, the above-mentioned contacting is performed in the presence of FP ligands (e.g., PGF2α), and said test compound blocks/inhibits the binding of said ligand to FP.

In another aspect, the present invention provides a method for determining whether a test compound may be useful for the treatment of a cancer of the gastrointestinal tract (e.g., colorectal cancer), the method comprising (a) contacting a test compound with a cell comprising a first nucleic acid comprising a transcriptionally regulatory element normally associated with a FP-modulated gene, operably linked to a second nucleic acid comprising a reporter gene capable of encoding a reporter protein; and (b) determining whether reporter gene expression or reporter protein activity is decreased in the presence of said test compound: wherein a decrease in said reporter gene expression or reporter protein activity is indicative that said test compound may be useful for the treatment of a cancer of the gastrointestinal tract.

In another aspect, the present invention provides a method (e.g., an in vitro method) for determining whether a test compound is an allosteric FP modulator with agonist or antagonist biased signaling properties (and thus may be used to prevent or treat a condition/disease associated with PGF2α and/or FP activity, as described above), said method comprising: (a) contacting said test compound with a cell expressing FP in the presence of PGF2α; (b) determining MAP kinase activity in said cell; and/or (c) determining RhoA/ROCK activity in said cell; wherein (i) an increased MAP kinase activity and/or (ii) a decrease RhoA/ROCK activity in said cell in the presence of said test compound relative to the absence thereof is indicative that said test compound is an allosteric FP antagonist.

In an embodiment, the above-mentioned MAP kinase activity is determined by measuring the relative activity of the protein kinase C (plasma membrane translocation) and/or phosphorylated ERK1/2 in said cell.

In another embodiment, the above-mentioned RhoA/ROCK activity is determined by measuring the extent of membrane ruffling in said cell.

The above-noted screening method or assay may be applied to a single test compound or to a plurality or "library" of such compounds (e.g., a combinatorial library). Any such compounds may be utilized as lead compounds and further modified to improve their therapeutic, prophylactic and/or pharmacological properties for preventing and/or treating a condition/disease associated with PGF2α and/or FP activity, such as cancer of the gastrointestinal tract (e.g., colorectal cancer).

Test compounds (drug candidates) may be obtained from any number of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means.

Screening assay systems may comprise a variety of means to enable and optimize useful assay conditions. Such means may include but are not limited to: suitable buffer solutions, for example, for the control of pH and ionic strength and to provide any necessary components for optimal activity and stability (e.g., protease inhibitors), temperature control means for optimal activity and/or stability, of the cells expressing FP, and detection means to enable the detection of the above-mentioned activity.

In an embodiment, the above-mentioned subject is a mammal, in a further embodiment a human. In an embodiment, the subject is a female.

The present invention is illustrated in further details by the following non-limiting examples.

Example 1

Chemistry

Figure 1:
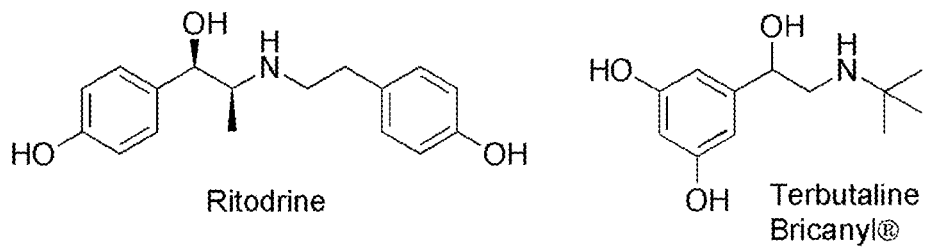
FIG. 1 shows representative currently used tocolytic drugs.
Figure 1:
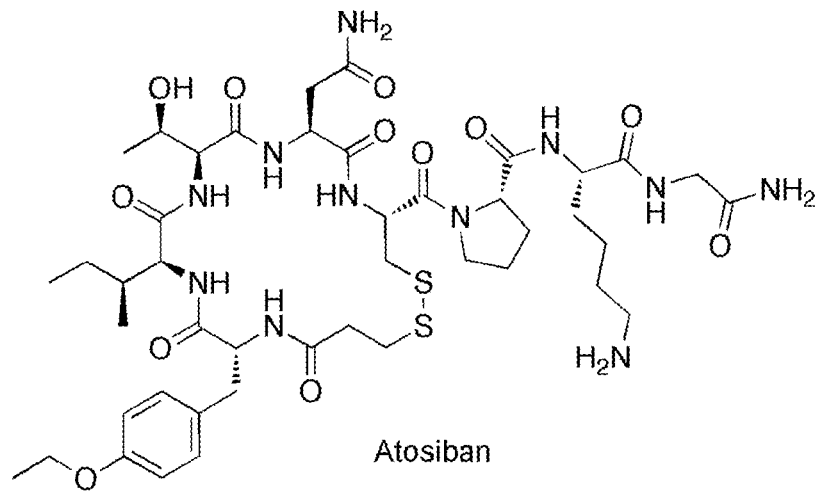
Figure 1:
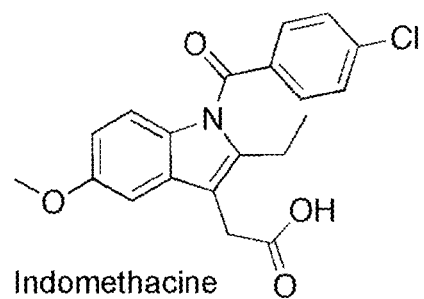
Figure 1:
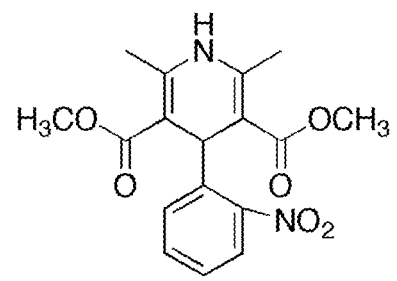
Figure 2:
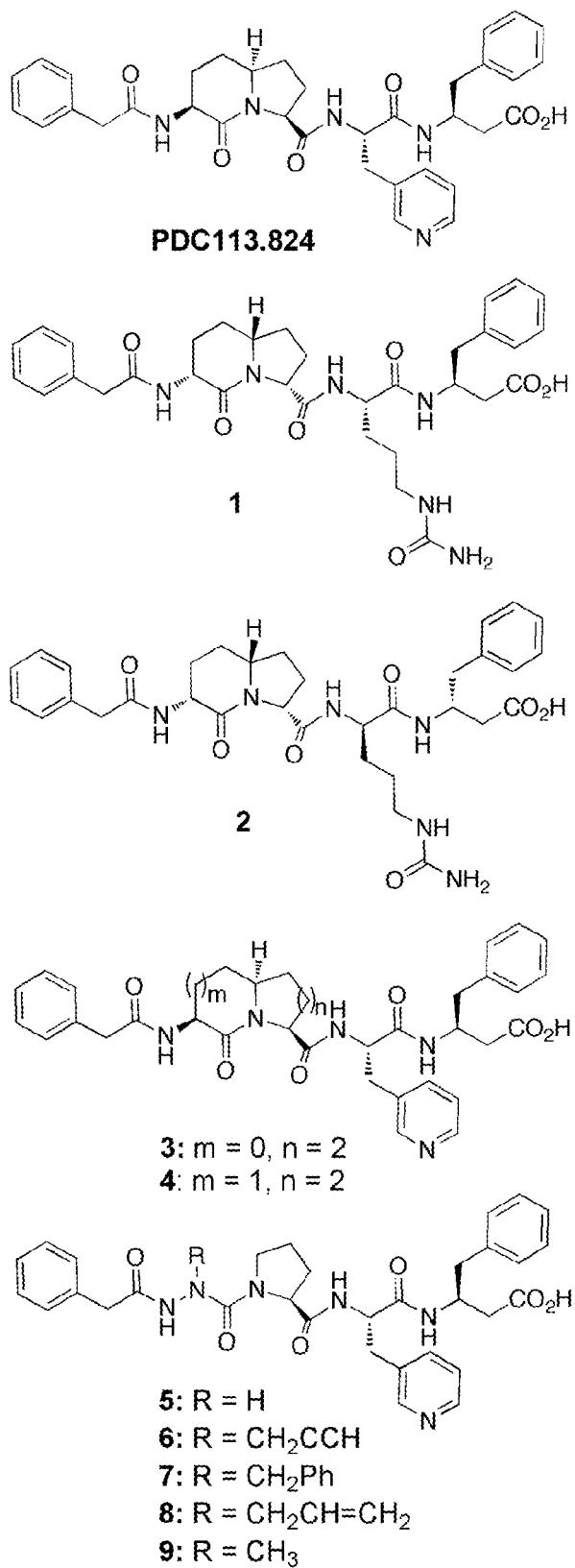
FIG. 2 shows the structure of PDC113.824, azabicycloalkanone mimics 1-4 and azapeptides 5-9.

In studies of the configuration and conformation of PDC113.824, the (3S,6S,9S)-I$^2$aa residue was replaced by its enantiomeric (3R,6R,9R)-I$^2$aa counterpart in mimic 1, as well as by (2S,6R,8S)-indolizidin-9-one(I$^9$aa, 3), and (2S,6R, 8S)-quinolizidinone amino acids (Qaa, 4, FIG. 2).[33]-37 In addition to these studies of the ring system, an enantiomeric analog (2) was prepared to examine the relationship between stereochemistry and activity.

Figure 3:
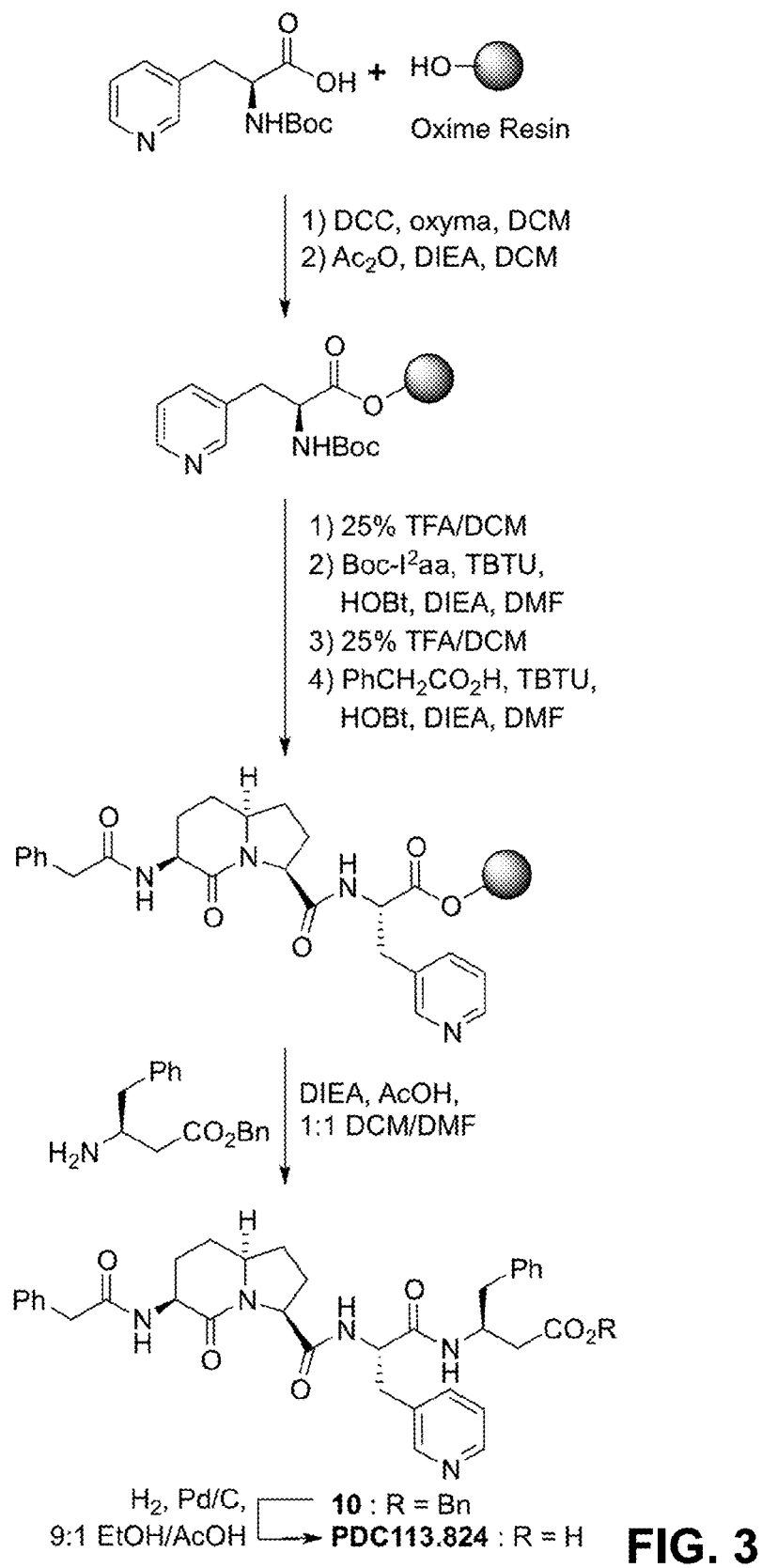
FIG. 3 shows steps in solid-phase synthesis of PDC113.824 (Scheme 1)

PDC113.824 and peptide mimics 1-4, all were synthesized on solid support using a Boc strategy on oxime resin as illustrated for the former in Scheme 1 (FIG. 3).[38] N-Boc-(3-Pyridyl)alanine [or N-(Boc)citruline] was coupled to the resin using dicyclohexylcarbodiimide (DCC) and Oxyma (EACNOx) in the presence of DIEA in dichloromethane.[39] After resin capping with acetic anhydride, the Boc group was removed with TFA in dichloromethane and the amine was free-based by washing the resin with DIEA in dichloromethane. The appropriate azabicyclo[X.Y.0]alkanone amino acid [(3S,6S,9S)- and (3R,6R,9R)-I$^2$aa, (2S,6R,8S)-I$^9$aa and (2S,6R,10S)-Qaa] was coupled using a mixture of TBTU/HOBt/DIEA in DMF for 3 h. Subsequent Boc group removal with TFA and coupling of phenyl acetic acid under similar conditions as mentioned above gave the N-terminal peptide linked to the resin, which was cleaved with (S)-β-homophenylalanine benzyl ester in presence of DIEA and acetic acid in dichloromethane to give the respective mimics as their corresponding esters. Benzyl ester cleavage was accomplished using hydrogen and palladium-on-carbon in a 9:1 ethanol acetic acid mixture to furnish the acids, which were purified by preparative reverse-phase HPLC (Table 3).

TABLE 3

| Entry | Compound | Retention time (system)$^a$ | Purity (%) | Retention time (system)$^b$ | Purity (%) |
|---|---|---|---|---|---|
| 1 | PDC113.824 | 9.77 (1) | 98.6 | 12.18 (3) | 95.5 |
| 2 | 1 | 7.83 (2) | 97.3 | 10.88 (4) | 95.6 |
| 3 | 2 | 7.77 (2) | 98.4 | 10.23 (4) | 96.7 |
| 4 | 3 | 5.59 (1) | 99.8 | 9.72 (4) | 95.7 |
| 5 | 4 | 4.92 (1) | 99.8 | 10.94 (4) | 97.2 |
| 6 | 5 | 6.88 (1) | 99.0 | 8.76 (3) | 97.1 |
| 7 | 6 | 7.96 (1) | 98.9 | 11.86 (3) | 98.5 |
| 8 | 7 | 8.84 (1) | 97.4 | 13.99 (3) | 98.9 |
| 9 | 8 | 8.20 (1) | 95.8 | 12.68 (3) | 98.7 |
| 10 | 9 | 7.77 (1) | 98.6 | 11.58 (3) | 99.0 |

Retention times (min) and purity were assessed using
$^a$ systems 1 or 2 eluting with a gradient of aqueous 0.1% formic acid (FA) in acetonitrile with 0.1% FA;
$^b$ systems 3 or 4 eluting with a gradient of aqueous 0.1% formic acid (FA) in methanol with 0.1% FA.

Figure 4:
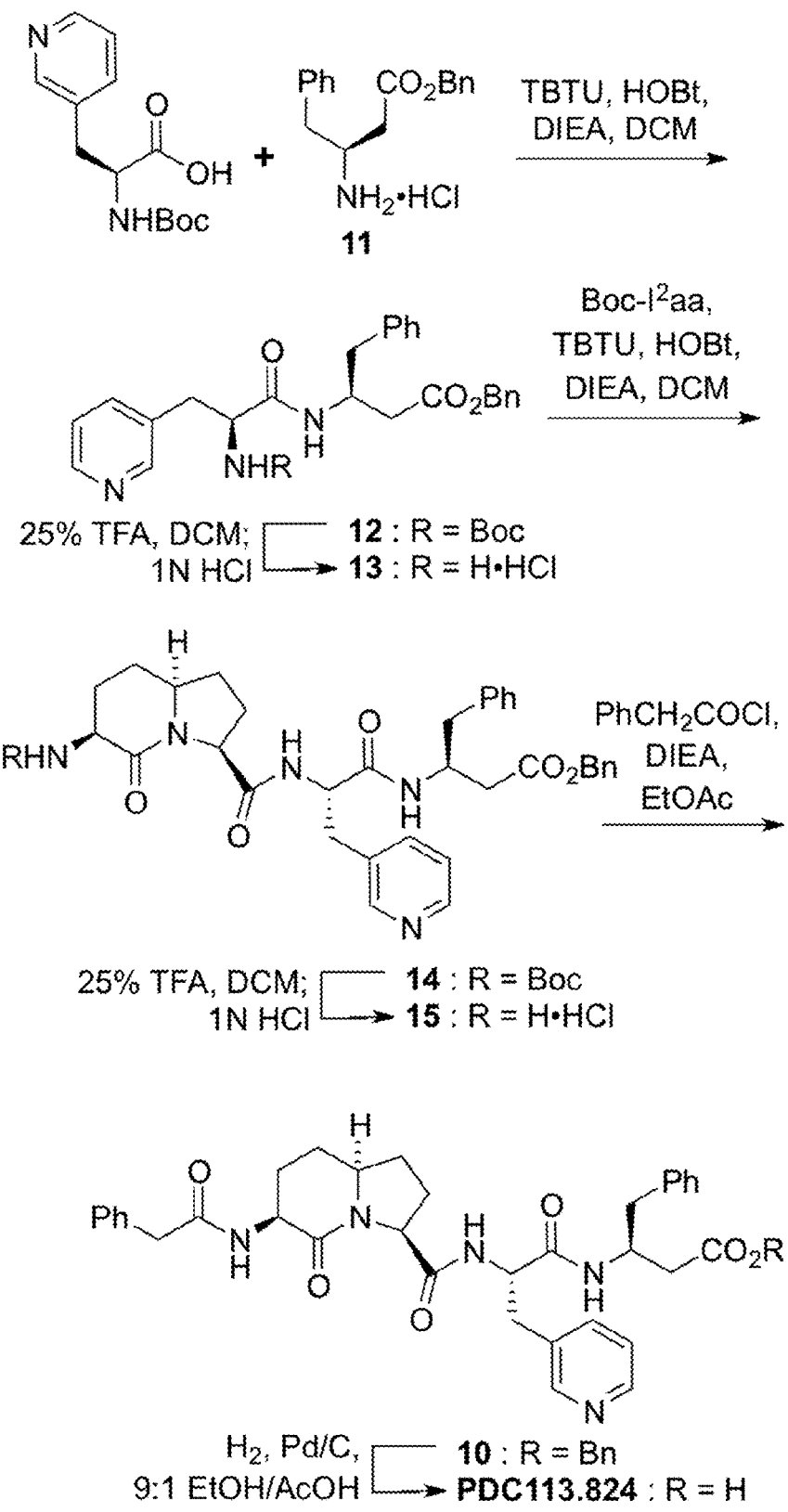
FIG. 4 shows steps in the solution-phase synthesis of PDC113.824 (Scheme 2)

A solution-phase method was developed for making PDC113.824 on larger scale (Scheme 2, FIG. 4). β-Homophenylalanine benzyl ester.hydrochloride 11 was obtained from Boc-β-homophenylalanine benzyl ester by removal of the Boc group using TFA in DCM, counter ion exchange by evaporation from aqueous HCl and freeze-drying. N-(Boc) Pyridylalanine was coupled to ester 11 using TBTU, HOBt and DIEA in dichloromethane to provide protected dipeptide 12 in 91% yield after chromatography. Using a similar protocol, the Boc group was removed with TFA and converted to amine hydrochloride 13, which was coupled with Boc-I$^2$aa to furnish amide 14 in 84% yield after chromatography. Removal of the Boc group from 14 and acylation of the resulting amine 15 with phenylacetyl chloride and DIEA in EtOAc gave benzyl ester 10, which was converted to PDC113.824 by hydrogenation as described above.

The azaGly-Pro dipeptide 16 was synthesized as previously described by acylation of proline using the activated methylidene carbazate prepared from reacting benzophenone hydrazone with p-nitrophenylchloroformate.[45] Hydrazone protected azaGly-Pro 16 was then coupled to pyridinylalaninyl-β-homophenylalanine benzyl ester 13 using TBTU, HOBt and DIEA to give the protected aza-tetrapeptide 17 in 70% yield after chromatography. Solvolysis with 1N HCl in THF converted semicarbazone ester 17 to its amino acid counterpart, which reacted with phenyl acetyl chloride to give AzaGly-Pro mimic 5, albeit in 20% overall yield after purification by preparative HPLC (Scheme 3, FIG. 5).

Four additional azapeptides 6-9 were prepared by a common route which featured alkylation of benzhydrylidene azaglycinyl proline tert-butyl ester as previously described, using a set of alkyl halides: propargyl bromide, benzyl bromide, allyl iodide and iodomethane (Scheme 4, FIG. 6).[46] Four alkyl groups were selected to probe the impact of aliphatic and aromatic side chains on the efficacy of the FP ligands. Selective removal of the benzhydrylidene protection from 18a-d without tert-butyl ester cleavage was accomplished using hydroxylamine hydrochloride in pyridine.[46] Acylation with phenyl acetyl chloride and tert-butyl ester removal with trifluoroacetic acid gave the N-terminal dipeptides 21a-d, which were subsequently activated as mixed anhydrides using iso-butylchloroformate and coupled to pyridinylalaninyl-(3-homophenylalanine benzyl ester 13 to give the desired benzyl ester protected azapeptides 22a-d in 40-55% yields. To avoid reduction of olefin side chains, ester hydrolysis was performed with lithium hydroxide in dioxane to give the aza-peptide mimics 6-9 in 66-85% yields.

Example 2

Materials and Methods

Chemistry—General Methods

Unless otherwise noted, reagents were obtained from commercial sources and used without further purification, and reactions were performed under an argon atmosphere using dry solvents transferred by syringe. Anhydrous solvents (THF, $CH_2Cl_2$, and $CH_3OH$) were obtained by passage through solvent filtration systems (GlassContour™, Irvine, Calif.). DIEA was distilled over ninhydrin and $CaH_2$. Final reaction mixture solutions were dried over $MgSO_4$ or $Na_2SO_4$. Column chromatography was carried out on 230-400 mesh silica gel, and TLC was on glass-backed silica plates. Specific rotations $[\alpha]_D$ were measured at 20° C. at the specified concentrations (c in g/100 mL) using a 1 dm cell length on a Perkin Elmer Polarimeter™341 and the general formula: $[\alpha]_D^{20}=(100\alpha)/(dc)$. Purity of all final products was determined by LC-MS and/or analytical HPLC to be ≥95%. HPLC purity of compounds was measured with a reverse phase HPLC (Phenomenex Gemini™ C18 column 4.6 mm×150 mm, 3 μm, 214 nm) with two different solvent systems. In system 1, the gradient of elution was 40% to 90% A/B over 20 min at a flow rate of 0.4 mL/min, in which solvent A was aqueous 0.1% formic acid (FA) and solvent B was acetonitrile with 0.1% FA. In system 2, the gradient of elution was 20% to 90% A/B over 20 min at a flow rate of 0.4 mL/min, where solvent A was aqueous 0.1% FA and solvent B was acetonitrile with 0.1% FA. In system 3, the gradient of elution was 40% to 90% A/B over 20 min at a flow rate of 0.4 mL/min, where solvent A was aqueous 0.1% FA and solvent B was methanol with 0.1% FA. In system 4, compounds were eluted using a gradient of elution of 60% to 90% A/B over 20 min at a flow rate of 0.4 mL/min, where solvent A was aqueous 0.1% FA and solvent B was methanol with 0.1% FA. Accurate mass measurements were performed on a LC-MSD-TOF instrument from Agilent™ technologies in positive electrospray mode for high-resolution mass spectrometry (HRMS) at the Université de Montréal Mass Spectrometry facility. Either protonated molecular ions $[M+H]^+$ or sodium adducts $[M+Na]^+$ were used for empirical formula confirmation. $^1H$ NMR spectra were measured in $CDCl_3$, $CD_3OD$ or DMSO-$d_6$ at 400 or 700 MHz and referenced to $CHCl_3$ (7.26 ppm), $CH_3$OD (3.31 ppm) or DMSO (2.50 ppm). $^{13}C$ NMR spectra were measured in $CDCl_3$, $CD_3OD$ or DMSO-$d_6$ at 100 MHz and respectively referenced to $CDCl_3$ (77.0 ppm), $CD_3OD$ (49.0 ppm) or DMSO (39.52 ppm). Coupling constant J values were measured in hertz (Hz) and chemical shift values in parts per million (ppm).

General Protocols for Solid-Phase Synthesis of Mimics

Oxime resin (1 g, 0.45 mmol) was swollen in methanol, filtered and swollen in dichloromethane (DCM). N-(Boc)-(3-pyridyl)alanine (150 mg, 0.56 mmol) [or N-(Boc)citruline (154 mg, 0.56 mmol)] diluted in a minimum of DCM was added to the swollen resin mixture, followed by 2-ethyl 2-(hydroxylimino) cyanoacetate (oxyma, 198 mg, 1.4 mmol), dicyclohexylcarbodiimide (DCC, 144 mg, 0.7 mmol) and DIEA (0.24 mL, 1.4 mmol). The resin mixture was shaken for 24 h at rt, filtered and washed with DCM (5×10 mL), EtOH (5×10 mL) and DCM (5×10 mL). Capping of the free sites of the resin was performed using acetic anhydride (0.2 mL, 2.2 mmol) and DIEA (0.175 mL, 1.1 mmol) in dichloromethane for 12 h at rt. The capped resin was filtered and washed with DCM (5×10 mL), 1:1 i-PrOH:DCM (v:v, 1×10 mL) and DCM (5×10 mL). Removal of the Boc protecting group was performed with 25% TFA in DCM (1×2 min and 2×15 min). The resin was washed with DCM (5×10 mL), 1:1 i-PrOH:DCM (v:v, 1×10 mL) and DCM (5×10 mL). The N-(Boc) amino azabicyclo[X.Y.0]alkanone carboxylic acid (prepared according to literature protocols,[33,36,37] 0.6 mmol) was sequentially coupled to the swollen resin using O-(benzotriazol-1-yl)-N,N,N',N'-tetramethyl uronium tetrafluoroborate (TBTU, 193 mg, 0.6 mmol) and hydroxybenzotriazole (HOBt, 81 mg, 0.6 mmol) in the presence of DIEA (0.21 mL, 1.2 mmol) in DMF for 3-5 h. After the coupling reaction, the resin was filtered and washed with DMF (2×10 mL), DCM (3×10 mL), 1:1 i-PrOH:DCM (v:v, 1×10 mL) and DCM (5×10 mL). The coupling reaction was monitored by the Kaiser test as well as by LC/MS analysis of product from cleavage of an aliquot of the resin with methoxyethylamine in chloroform. After Boc group removal as discussed above, phenyl acetic acid (82 mg, 0.6 mmol) was coupled to the swollen residue using the TBTU/HOBt protocol described above. Final resin cleavage was performed by treating the resin with the hydrochloride salt of (S)-β-homophenylalanine benzyl ester (161 mg, 0.6 mmol), DIEA (104 μL, 0.6 mmol) and AcOH (34 μL, 0.6 mmol) in DCM. After resin cleavage, the crude product was purified on a preparative reverse phase HPLC column (Phenomenex Gemini™ 5μ C18, 250×21.2 mm) using a solvent gradient from 20-80% acetonitrile (containing 0.1% TFA) in water (containing 0.1% TFA) to afford the desired peptide mimic benzyl ester 5 (20-40% yield). Hydrogenation of benzyl ester (0.09 mmol) with hydrogen (1 atm) was performed using palladium-on-activated-carbon (10% by wt, 10 mg) in EtOH (15 mL) for 5-8 h. The catalyst was filtered onto Celite™ and washed with methanol. The filtrate and washings were combined and evaporated to the acid, which was isolated by preparative HPLC (Phenomenex Gemini™5μ C18, 250×21.2 mm) using a gradient from 20-80% acetonitrile (containing 0.1% TFA) in water (containing 0.1% TFA) to afford the targeted mimics.

Phenylacetyl-(3S,6S,9S)-I²aa-(2S)-(3-pyridyl)alaninyl-(3S)-β-homophenylalanine PDC113.824: 5 mg, 2% yield. $^1H$ NMR (700 MHz, $D_2O$) δ1.43-1.54 (m, 2H), 1.65-1.68 (m, 1H), 1.72-1.76 (m, 1H), 2.01-2.12 (m, 4H), 2.36-2.39 (m, 1H), 2.54-2.56 (m, 1H), 2.65-2.68 (dd, J=9.3, 14 Hz, 1H), 2.87-2.89 (dd, J=5.2, 14.0 Hz, 1H), 3.02-3.05 (m, 1H), 3.10-3.13 (dd, J=6.4, 14.5 Hz, 1H), 3.56 (s, 2H), 3.59-3.63 (m, 1H), 4.24 (d, J=9.2 Hz, 1H), 4.35-4.38 (m, 2H), 4.49 (t, J=6.4 Hz, 1H), 7.22-7.32 (m, 10H), 7.86 (s, 1H), 8.27 (d, J=6.9 Hz, 1H), 8.47 (s, 1H), 8.55 (s, 1H). HRMS m/z calculated for $C_{35}H_{40}N_5O_6$ $[M+H]^+$ 626.2973. found 626.2972. Purity was assessed by RP-HPLC system 1: >98%, $t_R$=9.77. RP-HPLC system 3: >96%, $t_R$=12.18 min.

Phenylacetyl-(3R,6R,9R)-I²aa-(2S)-citrullinyl-(3S)-β-homophenylalanine (1): m=2.5 mg, 1% yield. HRMS m/z calculated for $C_{33}H_{43}N_6O_7$ $[M+H]^+$ 635.3188. found 635.3181. RP-HPLC system 1: 97.3%, $t_R$=7.83 min. RP-HPLC system 4: 95.6%, $t_R$=10.88 min.

Phenylacetyl-(3R,6R,9R)-I²aa-(2R)-3-citrullinyl-(3R)-β-homophenylalanine (2): m=1.5 mg, 1% yield. HRMS m/z calculated for $C_{33}H_{43}N_6O_7$ [M+H]$^+$ 635.3188. found 635.3188. RP-HPLC system 1: 98.4%, $t_R$=7.86 min. RP-HPLC system 4: 96.7%, $t_R$=10.89 min.

Phenylacetyl-(2S,6R,8S)-I$^9$aa-(2S)-(3-pyridyl)alaninyl-(3S)-β-homophenylalanine (3): m=5 mg, 2% yield. HRMS m/z calculated for $C_{35}H_{40}N_5O_6$ [M+H]$^+$ 626.2973. found 626.2984. RP-HPLC system 1: 100%, $t_R$=5.59 min. RP-HPLC system 3: 95.7%, $t_R$=10.23 min.

Phenylacetyl-(3S,6R,10S)-Qaa-(2S)-(3-pyridyl)alaninyl-(3S)-β-homophenylalanine (4): m=3 mg, 4% yield. HRMS m/z calculated for $C_{36}H_{42}N_5O_6$ [M+H]$^+$ 640.3130. found 640.3135. RP-HPLC system 1: 100%, $t_R$=4.92 min. RP-HPLC system 3: 97.2%, $t_R$=9.72 min.

N-Boc-(2S)-(3-pyridyl)alaninyl-(3S)-β-homophenylalanine benzyl ester (12): (3S)-N-(Boc)-β-Homophenylalanine (237 mg, 1 eq., 0.85 mmol, prepared from Boc-Phe according to the literature procedure[50]) was dissolved in 15 mL of acetonitrile and treated with cesium carbonate (1 eq., 277 mg) diluted in a minimum volume of water. The mixture was stirred for 1 h, treated drop-wise with benzyl bromide (0.15 mL, 1.5 eq., 1.27 mmol), stirred overnight and concentrated under reduced pressure. The residue was dissolved in EtOAc and washed successively with 0.1N HCl, sat. NaHCO$_3$ and brine, dried over Na$_2$SO$_4$ and concentrated under vacuum. The residue was purified by flash chromatography on silica gel (hexane/EtOAc, 9:1) to afford 253 mg of (3S)-N-(Boc)-β-homophenylalanine benzyl ester in 81% yields. $R_f$=0.37 (hexane/EtOAc 4:1); [α]$_{25}^D$ −18° (c 1.0, CHCl$_3$); $^1$H NMR (400 MHz, CDCl$_3$) δ1.43 (s, 9H), 2.51-2.56 (dd, J=5.5, 12.1 Hz, 1H), 2.82-2.98 (m, 2H), 4.22 (m, 1H), 5.11 (d, J=12.3 Hz, 1H), 5.14 (d, J=12.3 Hz, 1H), 7.15-7.40 (m, 10H); $^{13}$C NMR (100 MHz, CDCl$_3$) δ 28.8, 30.1, 38.1, 40.7, 49.3, 66.9, 79.8, 127.0, 128.8, 128.9, 129.0, 129.8, 136.1, 138.1, 155.5, 171.9. HRMS m/z calculated for $C_{22}H_{27}N_1O_4Na$ [M+Na]$^+$ 392.1832. found 392.1841.

(3S)-N-(Boc)-β-Homophenylalanine benzyl ester (144 mg, 0.39 mmol) was treated with a solution of 25% TFA in CH$_2$Cl$_2$ for 2-3 h at rt, when TLC showed complete disappearance of starting material ($R_f$=0.92, 10% MeOH in DCM). The reaction mixture was evaporated under reduced pressure. The residue was dissolved and co-evaporated three times from dichloromethane, and then diluted in 10 mL of 1N HCl, let stand for 1 h, and freeze-dried to afford (3S)-β-homophenylalanine benzyl ester hydrochloride 11 [113 mg (95%)] as white foam: $R_f$=0.38 (10% MeOH/CH$_2$Cl$_2$); [α]$_{25}^D$ 95.1° (c 0.25, CH$_3$OH); $^1$H NMR (400 MHz, CDCl$_3$) δ1.45 (br, 2H), 2.37-2.44 (dd, J=8.8, 16 Hz, 1H), 2.55-2.60 (dd, J=4.4, 16 Hz, 1H), 2.61-2.67 (dd, J=8.4, 13.6 Hz, 1H), 2.76-2.81 (dd, J=5.6, 13.6 Hz, 1H), 3.53 (m, 1H), 5.16 (s, 2H), 7.20-7.39 (m, 10H); $^{13}$C NMR (100 MHz, CDCl$_3$) δ30.1, 42.4, 50.1, 66.7, 126.9, 128.7, 128.9, 129.0, 129.7, 136.2, 138.9, 172.6. HRMS m/z calculated for $C_{17}H_{20}NO_2$ [M+H]$^+$ 270.1489. found 270.1488.

N-Boc-(2S)-(3-pyridyl)alanine (221 mg, 1.2 eq. 0.83 mmol) was dissolved in 5 mL of CH$_2$Cl$_2$, treated with HOBt (1.2 eq., 112 mg) and TBTU (1.2 eq., 226 mg), stirred at rt for 15 min, treated with a solution of (3S)-β-homophenylalanine benzyl ester hydrochloride (7, 210 mg, 1 eq., 0.69 mmol) in 5 mL of CH$_2$Cl$_2$ followed by DIEA (0.24 mL, 2 eq., 1.38 mmol), stirred for 3 h and evaporated under reduced pressure. The residue was purified by flash chromatography on silica gel using ethyl acetate as eluent to afford 325 mg (91%) of N-Boc-(2S)-(3-pyridyl)alaninyl-(3S)-β-homophenylalanine benzyl ester 12 as white foam: $R_f$=0.52 (10% MeOH/ CH$_2$Cl$_2$); [α]$_{25}^D$ −17° (c 1.55, CHCl$_3$). $^1$H NMR (400 MHz, CDCl$_3$) δ1.36 (s, 9H), 2.42 (d, J=4.9 Hz, 1H), 2.74 (dd, J=8.0, 10.5 Hz, 1H), 2.88 (m, 2H), 3.05 (dd, J=6.3, 13.9 Hz, 1H), 4.31 (m, 1H), 4.44 (m, 1H), 5.05 (d, J=12.2 Hz, 1H), 5.12 (d, J=12.2 Hz, 1H), 5.20 (d, J=8.1 Hz, 1H), 6.90 (m, 1H), 7.07-7.08 (m, 2H), 7.18-7.23 (m, 5H), 7.32-7.35 (m, 5H), 7.57 (d, 1H), 8.41 (s, 2H); $^{13}$C NMR (100 MHz, CDCl$_3$) δ27.9, 31.3, 36.6, 39.4, 47.1, 61.3, 66.1, 71.5, 123.1, 126.4, 128.0, 128.1, 128.2, 128.9, 135.2, 136.6, 136.9, 147.5, 147.9, 150.0, 169.9, 170.9, 171.0. HRMS m/z calculated for $C_{30}H_{36}N_3O_5$ [M+H]$^+$ 518.2649. found 518.2667.

(2S)-(3-Pyridyl)alaninyl-(3S)-β-homophenylalanine benzyl ester hydrochloride (13) N-Boc-(2S)-(3-Pyridyl)alaninyl-(3S)-β-homophenylalanine benzyl ester (12, 145 mg, 0.28 mmol) was treated with a solution of 25% TFA in CH$_2$Cl$_2$ for 2-3 h at rt, when complete disappearance of starting material was observed by TLC ($R_f$=0.52, 10% MeOH in DCM). The reaction mixture was evaporated under reduced pressure. The residue was co-evaporated three times with dichloromethane, and then diluted in 10 mL of 1N HCl, let stand for 1 h, and freeze-dried to afford 113 mg (96%) of hydrochloride 13 as fluffy white solid: $R_f$=0.16 (10% MeOH/ CH$_2$Cl$_2$); [α]$_{25}^D$ −60° (c 0.55, CH$_3$OH). $^1$H NMR (400 MHz, CH$_3$OD) δ 2.51-2.57 (dd, J=8, 16 Hz, 1H), 2.59-2.65 (dd, J=4.4, 15.6 Hz, 1H), 2.79-2.84 (dd, J=7.6, 13.2 Hz, 1H), 2.96-3.01 (dd, J=6.4, 13.6 Hz, 1H), 3.24-3.28 (dd, J=7.2, 14.4 Hz, 1H), 3.42-3.47 (dd, J=5.6, 18.4 Hz, 1H), 4.35 (t, J=6.4 Hz, 1H), 4.50 (m, 1H), 5.10 (q, J=12.4 Hz, 2H), 7.22-7.32 (m, 8H), 7.35-7.37 (m, 2H), 8.02 (m, 1H), 8.61 (d, J=Hz, 1H), 8.78 (m, 2H); $^{13}$C NMR (100 MHz, CH$_3$OD) δ34.2, 37.6, 40.1, 48.9, 53.4, 65.6, 126.8, 127.2, 128.2, 128.3, 128.6, 128.7, 129.5, 135.5, 136.5, 137.9, 141.0, 142.7, 148.6, 167.0, 171.5. HRMS m/z calculated for $C_{25}H_{28}N_3O_3$ [M+H]$^+$ 418.2125. found 418.2126.

N-Boc-(3S,6S,9S)-I$^2$aa-(2S)-(3-pyridyl)alaninyl-(3S)-β-homophenylalanine benzyl ester (14). A solution of Boc-I$^2$aa (75 mg, 1 eq., 0.25 mmol, prepared according to ref 46) in dichloromethane (5 mL) was treated with HOBt (34 mg, 1 eq.) and TBTU (80 mg, 1 eq.). After stirring for 15 min, the mixture was treated with dipeptide hydrochloride 13 (112 mg, 1 eq., 0.25 mmol), followed by DIEA (87 µL, 2 eq., 0.5 mmol), and stirred at rt for 6 h. Evaporation of the volatiles gave a residue, which was purified by flash chromatography on silica gel using 5% MeOH in DCM as eluant. Evaporation of the collected fractions afforded 146 mg (0:21 mmol, 84%) of benzyl ester 14 as pale yellow foam. $R_f$=0.42 (10% MeOH/ CH$_2$Cl$_2$); [α]$_{25}^D$ −41.5 (c 0.65, CHCl$_3$). $^1$H NMR (400 MHz, CDCl$_3$) δ1.29-1.44 (m, 3H), 1.47 (s, 9H), 1.81-1.87 (m, 1H), 1.97-2.07 (m, 2H), 2.26-2.32 (m, 2H), 2.52 (d, J=5.6 Hz, 2H), 2.79-2.84 (dd, J=8, 13.6 Hz, 1H), 2.86-2.99 (m, 2H), 3.16-3.21 (dd, J=4.8, 14.4 Hz, 1H), 3.49-3.54 (m, 1H), 4.07-4.13 (q, J=8 Hz, 1H), 4.37 (d, J=8.8 Hz, 1H), 4.47-4.52 (m, 1H), 4.55-4.59 (m, 1H), 5.09 (d, J=12.4 Hz, 1H), 5.12 (d, J=12.4 Hz, 1H), 5.85 (d, J=6.8 Hz, 1H), 7.06 (d, J=8 Hz, 1H), 7.13-7.22 (m, 6H), 7.26-7.40 (m, 5H), 7.54 (d, J=6.4 Hz, 1H), 7.66 (d, J=8 Hz, 1H), 8.39 (s, 1H), 8.45 (d, J=4.8 Hz, 1H). $^{13}$C NMR (100 MHz, CDCl$_3$) δ20.9, 25.3, 28.6, 34.7, 38.0, 40.5, 47.1, 48.2, 54.4, 61.5, 62.3, 66.7, 123.8, 126.9, 128.8, 128.6, 128.7, 128.8, 128.9, 130.3, 130.4, 132.2, 133.6, 136.2, 137.3, 138.1, 148.2, 150.7, 151.4, 154.6, 169.6, 170.1, 171.5, 172.5. HRMS m/z calculated for $C_{39}H_{48}N_5O_7$ [M+H]$^+$ 698.3548. found 698.3541.

(3S,6S,9S)-I$^2$aa-(2S)-(3-pyridyl)alaninyl-(3S)-4-homophenylalanine benzyl ester hydrochloride (15). N-Boc-(3S,6S,9S)-I$^2$aa-(2S)-(3-pyridyl)alaninyl-(3S)-β-homophenylalanine benzyl ester 14 (50 mg, 1 eq., 72 µmol) was treated with a solution of 25% TFA in CH$_2$Cl$_2$ for 2 h at rt. Evaporation of the volatiles under reduced pressure, followed by co-evaporation three more times from dichloromethane gave a residue, which was purified by preparative HPLC using a reverse phase C18 column as described in general methods. Freeze-drying of the collected fractions gave amino ester 15 (32 mg, 77%) as a fluffy white solid. $R_f$=0.2 (10% MeOH/CH$_2$Cl$_2$); $[\alpha]_D$=53° (c 0.65, CH$_3$OH). $^1$H NMR (400 MHz, CDCl$_3$) δ1.41-1.60 (m, 2H), 1.80-2.10 (m, 5H), 2.30 (m, 1H), 2.55 (m, 2H), 2.79-2.99 (m, 3H), 3.13 (m, 1H), 3.49 (m, 1H), 3.78 (m, 1H), 4.39 (m, 1H), 4.51 (m, 1H), 4.64 (m, 1H), 5.04 (d, J=12.4 Hz, 1H), 5.09 (d, J=12.4 Hz, 1H), 6.91 (m, 2H), 7.08-7.42 (m, 12H), 7.55 (s, 1H), 7.98 (s, 1H), 8.36 (s, 1H), 8.48 (s, 1H); $^{13}$C NMR (100 MHz, CDCl$_3$) δ26.3, 28.8, 32.2, 34.7, 37.9, 40.3, 48.1, 54.9, 58.5, 60.0, 66.9, 109.4, 127.0, 128.7, 128.9, 129.0, 129.7, 136.1, 137.9, 138.0, 170.5, 171.4, 171.8 HRMS m/z calculated for C$_{34}$H$_{41}$N$_5$O$_5$ [M+H]$^+$ 598.3024. found 598.3011.

Phenylacetyl-(3S,6S,9S)-I$^2$aa-(2S)-(3-pyridyl)alaninyl-(3S)-β-homophenylalanine benzyl ester (10). A solution of phenylacetyl chloride (3.2 µL, 1.2 eq., 24 µmol) was added to amine 15 (14 mg, 1 eq., 20 µmol) dissolved in 10 mL of dichloromethane followed by DIEA (7 µL, 2 eq., 40 µmol) and stirred at rt for 6 h. Evaporation of the volatiles gave a residue, which was purified by preparative HPLC to afford 11.4 mg (80%) of ester 10 as yellow oil. $[\alpha]_D$ -37° (c 0.75, CHCl3. $^1$H NMR (400 MHz, CDCl$_3$) δ1.27-1.35 (m, 3H), 1.84 (m, 1H), 1.98-2.05 (m, 2H), 2.25-2.32 (m, 2H), 2.55 (d, J=5.6 Hz, 2H), 2.82-2.95 (m, 3H), 3.13 (dd, J=4.0, 14.4 Hz, 1H), 3.49-3.54 (m, 1H), 3.68 (s, 1H), 4.30-4.38 (m, 2H), 4.46-4.55 (m, 2H), 5.10 (d, J=12 Hz, 1H), 5.13 (d, J=12 Hz, 1H), 7.08-7.39 (m, 18H), 7.55 (d, J=6.4 Hz, 1H), 7.72 (d, J=7.6 Hz, 1H), 8.38 (s, 2H); $^{13}$C NMR (100 MHz, CDCl$_3$) δ 27.0, 27.5, 27.7, 30.1, 32.5, 37.7, 40.4, 44.0, 47.8, 49.2, 55.2, 58.2, 59.9, 66.9, 127.1, 127.6, 128.7, 128.8, 128.9, 129, 129.3, 129.7, 129.8, 135.3, 136.1, 137.9, 170.2, 171.3, 171.7, 171.0 HRMS m/z calculated for C$_{42}$H$_{46}$N$_5$O$_6$ [M+H]$^+$ 716.3442. found 716.3438.

Benzhydrylidene aza-glycinyl-(2S)-prolyl-(2S)-3-pyridinylalaninyl-(3S)-β-homophenylalanine benzyl ester (17). A solution of benzhydrylidene aza-glycinyl-(2S)-proline (16, 93 mg, 0.28 mmol) in 10 mL of dichloromethane was treated with HOBt (37 mg, 0.28 mmol) and TBTU (89 mg, 0.28 mmol). After stirring for 10 min, the mixture was treated with (3-pyridyl)alaninyl-β-homophenylalaninyl benzyl ester hydrochloride (13, 125 mg, 0.28 mmol) and DIEA (144 µL, 0.828 mmol), and stirred for 6-8 h. Evaporation of the volatiles gave a residue, which was purified by flash chromatography on silica gel using 5% MeOH in DCM as eluant. Evaporation of the collected fractions afforded benzyl ester 17 (120 mg, 0.19 mmol, 70%) of as yellow oil. $R_f$=0.53 (10% MeOH/CH$_2$Cl$_2$); $[\alpha]_{25}^D$ -74.4° (c 1.25, CHCl$_3$). $^1$H NMR (400 MHz, CDCl$_3$) δ1.71-1.84 (m, 3H), 1.91-2.03 (m, 1H), 2.44-2.56 (m, 2H), 2.73-2.90 (m, 3H), 3.10-3.19 (m, 3H), 4.39 (m, 1H), 4.47-4.58 (m, 2H), 5.02 (d, J=12.4 Hz, 1H), 5.06 (d, J=12.4 Hz, 1H), 7.06-7.20 (m, 6H), 7.23-7.36 (m, 12 H), 7.48-7.56 (m, 6H), 7.77 (s, 1H), 8.28 (s, 1H), 8.31 (d, J=4 Hz, 1H); $^{13}$C NMR (100 MHz, CDCl$_3$) δ20.9, 25.3, 28.6, 34.7, 38.0, 40.5, 48.2, 54.4, 61.5, 66.7, 123.8, 126.9, 127.8, 128.6, 128.7, 128.8, 128.9, 130.3, 130.4, 132.2, 133.6, 136.2, 137.3, 138.1, 148.2, 150.7, 151.4, 154.6, 169.6, 170.1, 171.5, 172.5 HRMS m/z calculated for C$_{44}$H$_{45}$N$_6$O$_5$ [M+H$^+$] 737.3446. found 737.3455.

Phenylacetyl-aza-glycinyl-(2S)-prolyl-(2S)-3-pyridinylalaninyl-(3S)-β-homophenylalanine (5). Benzyl ester 13 (60 mg, 81.5 µmol) in 5 mL of THF was treated with 5 mL of 1N HCl at 60° C. for 12-24 h, when LC/MS analysis showed total conversion of 17 to azaglycinyl-prolinyl-(3-pyridyl)alaninyl-β-homophenylalanine ([M+H]$^+$=483). The volatiles were evaporated. The residue was dissolved in 5 mL of dichloromethane, treated with phenylacetyl chloride (11 µL, 81.5 µmol) and DIEA (42.5 µL, 0.25 mmol), stirred for 3-4 h, and evaporated to dryness. Purification was performed by preparative HPLC (Phenomenex Gemini 5µ C18, 250×21.2 mm) using a gradient from 10-90% methanol (containing 0.1% TFA) in water (containing 0.1% TFA) to afford 10 mg (21%) of azapeptide 5. $^1$H NMR (700 MHz, D$_2$O) δ1.51-1.54 (m, 1H), 1.65 (m, 1H), 1.82-1.86 (m, 1H), 2.00-2.05 (m, 1H), 2.28-2.33 (m, 2H), 2.46-2.49 (dd, J=4.8, 15.8 Hz, 1H), 2.63-2.66 (dd, J=5.0, 13.9 Hz, 1H), 2.89-2.93 (dd, J=9.0, 14.4 Hz, 1H), 2.98-3.01 (dd, J=6.3, 14.5 Hz, 1H), 3.24-3.28 (dd, J=7.6, 9.3 Hz, 1H), 3.35-3.38 (m, 1H), 3.51 (d, J=15.1 Hz, 1H), 3.55 (d, J=15.1 Hz, 1H), 4.11 (dd, J=4.1, 8.8 Hz, 1H), 4.22 (m, 1H), 4.38 (dd, J=6.4, 8.9 Hz, 1H), 7.06-7.72 (m, 10H), 7.74 (t, J=6.7 Hz, 1H), 8.12 (d, J=8.0 Hz, 1H), 8.31 (s, 1H), 8.40 (d, J=5.0 Hz, 1H); $^{13}$C NMR (175 MHz, D$_2$O) δ 26.3, 29.6, 33.7, 38.9, 39.9, 40.0, 46.2, 48.4, 53.6, 60.7, 126.6, 126.9, 127.3, 127.8, 128.4, 128.9, 129.1, 129.2, 129.4, 133.9, 137.4, 137.9, 139.6, 140.4, 147.3, 157.2, 170.3, 174.9, 175.1, 175.2. HRMS m/z calculated for C$_{32}$H$_{37}$N$_6$O$_6$ [M+H]$^+$ 601.2769 found 601.2772. RP-HPLC system 1: 99%, $t_R$=6.88 min. RP-HPLC system 3: 97.1%, $t_R$=8.76 min.

Aza-propargylglycinyl-proline tert-butyl ester (19a). As reported for the synthesis of 19b in reference 46, benzhydrylidene aza-propargylglycinyl-proline tert-butyl ester 18a (100 mg, 0.23 mmol) was stirred with hydroxylamine hydrochloride (29 mg, 0.42 mmol) in 20 mL of pyridine overnight at 60° C. The volatiles were removed by rotary evaporation followed by co-evaporation with dichloromethane and ethyl acetate until solidification. Purification by flash chromatography on silica gel using a 1:1 mixture of ethyl acetate in hexane afforded amine 19a (51.3 mg, 84%) as a pale yellow foam: $R_f$=0.39 (hexane/EtOAc 1:1); $[\alpha]^{20}_D$ -48° (c 1.15, CHCl$_3$). $^1$H NMR (CDCl$_3$, 400 MHz) δ 1.46 (s, 9H), 1.84-1.99 (m, 3H), 2.13-2.20 (m, 1H), 2.31 (s, 1H), 3.64 (m, 2H), 4.16 (d, J=17.2 Hz, 1H), 4.24 (d, J=17.2 Hz, 1H), 4.43 (m, 1H); $^{13}$C NMR (CDCl$_3$, 100 MHz) δ23.3, 27.6, 30.1, 42.6, 48.8, 61.5, 73.0, 78.1, 80.3, 159.8, 172.5. HRMS m/z calculated for C$_{13}$H$_{21}$N$_3$O$_3$ Na [M+Na]$^+$ 290.1475. found 290.1488.

Aza-phenylalaninyl-proline tert-butyl ester (19b) was prepared according to the procedure described in reference 46 from benzhydrylidene aza-phenylalaninyl-proline tert-butyl ester 18b (50 mg, 0.1 mmol). Purification of the residue by flash chromatography on silica gel using a 1:1 mixture of ethyl acetate in hexane afforded amine 19b (28 mg, 88%) as a pale yellow foam: $R_f$=0.31 (hexane/EtOAc 1:1); $[\alpha]^{20}_D$ -35° (c 0.1, CHCl$_3$). $^1$H NMR (CDCl$_3$, 400 MHz): δ 1.44 (s, 9H), 1.83-1.95 (m, 3H), 2.12-2.19 (m, 1H), 3.64-3.67 (m, 2H), 4.46 (m, 1H), 4.59 (d, J=16 Hz, 1H), 4.61 (d, J=16 Hz, 1H), 7.28-7.35 (m, 5H); $^{13}$C NMR (CDCl$_3$, 100 MHz): δ23.4, 27.6, 30.1, 49.1, 56.1, 61.7, 80.1, 127.2, 127.3, 128.1, 128.3, 136.3, 172.7. HRMS (ESI) m/z calculated for C$_{17}$H$_{26}$N$_3$O$_3$ [M+H]$^+$ 320.1971. found, 320.1969.

Aza-allylglycinyl-proline tert-butyl ester (19c) was prepared according to the procedure described above from benzhydrylidene aza-allylglycinyl-proline tert-butyl ester 18c (191.9 mg, 0.43 mmol). Purification of the residue by flash chromatography on silica gel using a 1:1 mixture of ethyl acetate in hexane afforded amine 19c (54.5 mg, 47%) as a pale yellow foam: $R_f$=0.22 (EtOAc); $[\alpha]^{20}_D$ -38.5° (c 2.05, CHCl$_3$). $^1$H NMR (CDCl$_3$, 400 MHz): δ1.44 (s, 9H), 1.79-1.94 (m, 3H), 2.11-2.15 (m, 1H), 3.56-3.62 (m, 2H), 3.73 (br, 2H), 3.95 (d, J=5.0 Hz, 2H), 4.38-4.41 (dd, J=4.3, 8.4 Hz, 1H), 5.23-5.27 (m, 2H), 5.81-5.88 (m, 1H); $^{13}$C NMR (CDCl$_3$, 100 MHz): 823.4, 27.6, 30.0, 48.9, 55.4, 61.5, 80.1, 118.6, 132.6, 160.6, 172.6. HRMS m/z calculated for C$_{13}$H$_{24}$N$_3$O$_3$ [M+H]$^+$ 270.1812. found 270.1814.

Aza-alaninyl-(2S)-proline tert-butyl ester (19d) was prepared according to the procedure described above from benzhydrylidene aza-alalinyl-proline tert-butyl ester 18d (200 mg, 0.51 mmol). Purification of the residue by flash chromatography on silica gel using a 5% methanol in dichloromethane afforded amine 19d (59.5 mg, 48%) as a yellow oil: $R_f$=0.25 (5% MeOH/CH$_2$Cl$_2$); $[\alpha]^{20}_D$ −24° (c 3.03, CHCl$_3$). $^1$H NMR (CDCl$_3$, 400 MHz): δ 1.43 (s, 9H), 1.80-1.95 (m, 3H), 2.11-2.14 (m, 1H), 3.04 (s, 3H), 3.55 (t, J=6.8 Hz, 2H), 3.99 (br, 2H), 4.33-4.37 (dd, J=4.8, 8.0 Hz, 1H); $^{13}$C NMR (CDCl$_3$, 100 MHz): 823.6, 27.6, 29.9, 41.6, 45.6, 48.8, 80.2, 161.5, 172.6. HRMS m/z calculated for C$_{11}$H$_{22}$N$_3$O$_3$ [M+H]$^+$ 244.1656. found 244.1650.

Representative protocol for phenylacetylation of aza-dipeptide tert-butyl esters: Phenylacetyl-aza-propargylglycinyl-(2S)-proline tert-butyl ester (20a). Aza-propargylglycinylproline tert-butyl ester (19a, 60 mg, 0.23 mmol) was dissolved in 10 mL of EtOAc, treated with phenyl acetyl chloride (32 μL, 0.24 mmol) and DIEA (46 μL, 0.26 mmol), stirred 12 h, and washed with 10 mL of HCl 1N and 10 mL of brine. After evaporation of the volatiles the crude material was purified by chromatography on silica gel using a mixture of ethyl acetate in hexane (1:1) to afford ester 20a (85.5 mg, 98% yield) as yellow oil. $R_f$=0.32 (hexane/EtOAc 1:1); $[\alpha]^{20}_D$ 47.4° (c 1.9, CHCl$_3$); $^1$H NMR (400 MHz, CDCl$_3$) δ1.43 (s, 9H), 1.73-1.90 (m, 3H), 2.05-2.09 (m, 1H), 2.15 (t, J=2.4 Hz, 1H), 3.33 (m, 2H), 3.61 (s, 2H), 4.20-4.24 (m, 3H), 7.29-7.34 (m, 5H), 7.91 (s, 1H); $^{13}$C NMR (100 MHz, CDCl$_3$) δ25.2, 28.4, 30.0, 40.0, 42.1, 48.9, 61.8, 73.4, 78.6, 81.7, 127.9, 129.4, 129.6, 134.1, 158.8, 170.0, 172.4. HRMS m/z calculated for C$_{21}$H$_{27}$N$_3$O$_4$Na [M+Na]$^+$ 408.1894. found 408.1903.

Phenylacetyl-aza-phenylalaninyl-(2S)-proline tert-butyl ester (20b) was obtained from aza-dipeptide 19b (50 mg, 0.16 mmol) as described above in 60% yield as a yellow oil. $R_f$=0.31 (hexane/EtOAc 1:1); $[\alpha]_{25}^D$ 30.4° (c 1.25, CHCl$_3$); $^1$H NMR (400 MHz, CDCl$_3$) δ1.47 (s, 9H), 1.76-1.83 (m, 2H), 1.88-1.92 (m, 1H), 2.05-2.16 (m, 1H), 3.35-3.39 (m, 1H), 3.43-3.57 (m, 3H), 4.34 (t, J=7.2 Hz, 1H), 4.43 (d, J=14.2 Hz, 1H), 4.71 (d, J=14.2 Hz, 1H), 7.10-7.13 (m, 2H), 7.17-7.19 (m, 2H), 7.24-7.28 (m, 7H); $^{13}$C NMR (100 MHz, CDCl$_3$) δ24.7, 27.6, 29.2, 41.4, 48.4, 52.7, 61.1, 80.9, 127.0, 127.3, 128.1, 128.2, 128.6, 128.9, 129.0, 133.2, 135.5, 158.9, 168.9, 171.9. HRMS m/z calculated for C$_{25}$H$_{32}$N$_3$O$_4$ [M+H]$^+$ 438.2387. found 438.2379.

Phenylacetyl-aza-allylglycinyl-(2S)-proline tert-butyl ester (20c) was obtained from aza-dipeptide 19c (50 mg, 0.19 mmol) as described above in 90% yield as a yellow oil. $R_f$=0.25 (hexane/EtOAc 1:1); $[\alpha]_{25}^D$ 36.6° (c 1.75, CHCl$_3$); $^1$H NMR (400 MHz, CDCl$_3$) δ1.44 (s, 9H), 1.75-1.92 (m, 3H), 2.09-2.18 (m, 1H), 3.29-3.36 (m, 1H), 3.38-3.47 (m, 1H), 3.55 (s, 2H), 3.84-3.89 (dd, J=8, 16 Hz, 1H), 3.98-4.03 (dd, J=8, 16 Hz, 1H), 4.28 (t, J=7.2 Hz, 1H), 5.01 (dd, J=1.2, 16.8 Hz, 1H), 5.07 (dd, J=1.2, 10.0 Hz, 1H), 5.79 (m, 1H), 7.26-7.33 (m, 5H), 7.65 (s, 1H); $^{13}$C NMR (100 MHz, CDCl$_3$) δ25.5, 28.4, 30.0, 42.3, 49.1, 53.7, 61.7, 81.7, 120.1, 127.9, 129.3, 129.6, 132.7, 134.3, 159.7, 169.9, 172.6. HRMS m/z calculated for C$_{21}$H$_{29}$N$_3$O$_4$Na [M+Na]$^+$ 410.2050. found 410.2058.

Phenylacetyl-aza-alaninyl-(2S)-proline tert-butyl ester (20d) was obtained from aza-dipeptide 19d (59 mg, 0.24 mmol) as described above in 75% yield as a yellow oil. $R_f$=0.45 (EtOAc); $[\alpha]_{25}^D$ 27° (c 1.75, CHCl$_3$); $^1$H NMR (400 MHz, CDCl$_3$) δ1.45 (s, 9H), 1.74-1.78 (m, 2H), 1.86 (m, 1H), 2.11 (m, 1H), 3.01 (s, 3H), 3.29 (m, 1H), 3.37 (m, 1H), 3.56 (s, 2H), 4.24 (t, J=6.8 Hz, 1H), 7.28-7.33 (m, 5H), 8.28 (s, 1H); $^{13}$C NMR (100 MHz, CDCl$_3$) δ24.8, 27.6, 29.2, 38.3, 41.2, 48.4, 60.9, 80.9, 127.0, 128.5, 128.8, 133.7, 159.5, 168.9, 172.0. HRMS m/z calculated for C$_{19}$H$_{28}$N$_3$O$_4$ [M+H]$^+$ 362.2074. found 362.2074.

Representative Protocol for Azapeptide Benzyl Ester Synthesis:

Phenylacetyl-aza-propargylglycinyl-(2S)-prolyl-(2S)-3-pyridylalaninyl-(3S)-β-homophenylalanine benzyl ester (22a). Phenylacetyl-aza-propargylglycinyl-(2S)-proline tert-butyl ester (20a, 85 mg, 0.22 mmol) was treated with a solution of 9:1 TFA in dichloromethane and stirred 1 h at room temperature until complete disappearance of starting material. The mixture was then evaporated and co-evaporated 3 times with dichloromethane, then dissolved in EtOAc. The organic phase was extracted with saturated NaHCO$_3$ and the basic aqueous phase was acidified with 1N HCl then back-extracted with 5×10 mL of EtOAc. After evaporation of the volatiles, crude acid 21a was dissolved in THF (7 mL), cooled to −15° C. and treated sequentially with isobutyl chloroformate (31 μL, 0.242 mmol) and N-methyl morpholine (36 μL, 0.33 mmol), stirred for 15 min and treated with a solution of (3-pyridyl)alaninyl-β-homophenylalanine benzyl ester hydrochloride (13, 111 mg, 0.27 mmol) in ethyl acetate (5 mL). After stirring at −15° C. for 1 h, the volatiles were removed under reduced pressure and the crude material was purified by chromatography on silica gel using ethyl acetate as eluant to afford benzyl ester 22a (64 mg, 40% yield) as pale yellow foam. $R_f$=0.42 (10% MeOH/CH$_2$Cl$_2$); $[\alpha]_{25}^D$ 14.7° (c 1.5, CHCl$_3$); $^1$H NMR (400 MHz, CDCl$_3$) δ1.13-1.28 (m, 1H), 1.61-1.69 (m, 2H), 2.17 (m, 1H), 2.32 (s, 1H), 2.59-2.71 (m, 2H), 2.81-2.84 (m, 2H), 2.85-2.99 (m, 2H), 3.26 (d, J=12.8 Hz, 1H), 3.36 (t, J=8 Hz, 1H), 3.64-3.76 (m, 2H), 3.82 (d, J=17.2 Hz, 1H), 4.24-4.28 (dd, J=7.2, 10.4 Hz, 1H), 4.41 (d, J=16.8 Hz, 1H), 4.55 (m, 2H), 5.09 (dd, J=12.4, 17.6 Hz, 2H), 7.16 (m, 6H), 7.25-7.35 (m, 11H), 7.41 (d, J=7.6 Hz, 1H), 7.57 (d, J=8.4 Hz, 1H), 8.42 (s, 2H), 9.98 (s, 1H); $^{13}$C NMR (100 MHz, CDCl$_3$) δ26.1, 30.0, 30.1, 34.4, 38.9, 40.7, 41.2, 48.5, 50.4, 54.8, 63.4, 66.8, 74.5, 78.3, 123.8, 126.9, 128.0, 128.6, 128.7, 129.4, 129.7, 130.1, 134.2, 134.5, 136.1, 136.3, 136.8, 138.1, 148.1, 150.6, 160.3, 171.0, 171.1, 171.2, 172.1. HRMS m/z calculated for C$_{42}$H$_{45}$N$_6$O$_6$ [M+H]$^+$ 729.3395. found 729.3382.

Phenylacetyl-aza-phenylalaninyl-(2)-pry(2S)-3-pyridylalaninyl-(3S)-β-homophenylalanine benzyl ester (22b) was obtained from ester 20b (42 mg, 96 μmol) as described above in 48% yield as pale yellow foam. $R_f$=0.35 (10% MeOH/CH$_2$Cl$_2$); $[\alpha]_{25}^D$ 9.3° (c 1.4, CHCl$_3$); $^1$H NMR (400 MHz, CDCl$_3$) δ1.28 (m, 1H), 1.69-1.74 (m, 2H), 2.19-2.21 (m, 1H), 2.64-2.67 (m, 2H), 2.87-3.01 (m, 3H), 3.07 (m, 1H), 3.22 (d, J=12.4 Hz, 1H), 3.38 (t, J=8 Hz, 1H), 3.61 (s, 2H), 3.89 (d, J=13.6 Hz, 1H), 4.30-4.34 (dd, J=6.8, 10.2 Hz, 1H), 4.55-4.59 (m, 2H), 5.03-5.14 (m, 3H), 7.12-7.35 (m, 22H), 7.51 (d, J=7.2 Hz, 1H), 7.60 (d, J=8.8 Hz, 1H), 8.34 (br, 2H), 8.72 (s, 1H); $^{13}$C NMR (100 MHz, CDCl$_3$) δ25.4, 29.4, 33.5, 38.3, 40.0, 40.7, 47.7, 49.8, 53.7, 53.9, 62.7, 66.0, 126.0, 127.4, 127.7, 127.8, 127.9, 128.0, 128.1, 128.4, 128.7, 128.8, 128.9, 129.3, 132.9, 135.1, 135.6, 137.6, 160.3, 169.8, 169.9, 170.5, 171.3. HRMS m/z calculated for C$_{46}$H$_{49}$N$_6$O$_6$ [M+H]$^+$ 781.3708. found 781.3727.

Phenylacetyl-aza-allylglycinyl-(2S)-prolyl-(2S)-3-pyridylalaninyl-(3S)-β-homophenylalanine benzyl ester (22c) was obtained from ester 20c (66 mg, 0.17 mmol) as described above in 55% yield as yellow foam. $R_f$=0.40 (10% MeOH/CH$_2$Cl$_2$); $[\alpha]_{25}^D$ −10.6° (c 1.8, CHCl$_3$); $^1$H NMR (400 MHz, CDCl$_3$) δ1.27 (m, 1H), 1.67-1.74 (m, 2H), 2.16-2.21 (m, 1H), 2.59-2.70 (m, 2H), 2.82-2.96 (m, 3H), 3.02-3.08 (m, 1H), 3.27-3.37 (m, 2H), 3.54-3.59 (dd, J=8.8, 14.4 Hz, 1H), 3.68 (s, 2H), 4.28-4.32 (m, 2H), 4.54-4.59 (m, 2H), 5.05-5.15 (m, 4H), 5.68-5.77 (m, 1H), 7.19-7.21 (m, 6H), 7.28-7.36 (m, 11H), 7.52 (d, J=8 Hz, 1H), 7.58 (d, J=8 Hz, 1H), 8.43 (br, 2H), 8.69 (s, 1H); $^{13}$C NMR (100 MHz, CDCl$_3$) δ26.1, 30.1, 34.3, 39.0, 40.8, 41.6, 48.5, 50.4, 53.7, 54.7, 63.3, 66.8, 120.7, 126.8, 128.2, 128.5, 128.7, 128.8, 128.9, 129.5, 129.6, 130.0, 132.7, 133.9, 136.4, 138.4, 160.7, 170.6, 170.7, 171.2, 172.1. HRMS m/z calculated for C$_{42}$H$_{47}$N$_6$O$_6$ [M+H]$^+$ 731.5552. found 731.3541.

Phenylacetyl-aza-alaninyl-(2S)-prolyl-(2S)-3-pyridyl-alaninyl-(3S)-β-homophenylalanine benzyl ester (22d) was obtained from ester 20d (65 mg, 0.18 mmol) as described above in 40% yield as pale yellow foam. R$_f$=0.32 (10% MeOH/CH$_2$Cl$_2$); [α]$_{25}^D$ −19.6° (c 2.8, CHCl$_3$); $^1$H NMR (400 MHz, CDCl$_3$) δ1.27 (m, 1H), 1.67-1.70 (m, 2H), 2.15-2.17 (m, 1H), 2.63-2.71 (m, 2H), 2.81-2.84 (m, 2H), 2.86-2.97 (m, 5H), 3.22-3.32 (m, 2H), 3.67 (s, 2H), 4.25-4.29 (dd, J=6.8, 10.4 Hz, 1H), 4.52-4.60 (m, 2H), 5.09 (d, J=12.4 Hz, 1H), 5.13 (d, J=12.4 Hz, 1H), 7.17-7.19 (m, 6H), 7.27-7.42 (m, 13H), 7.58 (d, J=8.8 Hz, 1H), 8.35-8.43 (s, 1H), 9.27 (s, 1H); $^{13}$C NMR (100 MHz, CDCl$_3$) δ26.2, 29.9, 34.4, 39.2, 41.0, 41.4, 48.6, 50.3, 54.8, 63.4, 66.8, 126.8, 128.0, 128.5, 128.7, 128.9, 129.4, 129.5, 130.1, 136.4, 136.9, 138.4, 147.9, 161.4, 170.6, 171.3, 172.4. HRMS m/z calculated for C$_{40}$H$_{45}$N$_6$O$_6$ [M+H]$^+$ 705.3395. found 705.3392.

Phenylacetyl-aza-propargylglycinyl-(2S)-prolyl-(2S)-3-(pyridyl)-alaninyl-(3S)-β-homophenylalanine (6). Phenylacetyl-aza-propargylglycinyl-(2S)-prolyl-(2S)-3-pyridyl-alaninyl-(3S)-β-homophenylalanine benzyl ester (22a, 25 mg, 0.034 mmol) was dissolved in a minimum amount of dioxane, cooled to 0° C., treated with a 2N LiOH (5 mL), stirred for 30 min, and the volatiles were evaporated under reduce pressure. The aqueous residue was acidified to pH 5 using 1N HCl and extracted with ethyl acetate. The organic extractions were combined, dried with sodium sulfate and concentrated under vacuum. The residue was purified by preparative HPLC, on a C18 reverse-phase column, using methanol in water as eluant. Freeze-drying of the collected fractions gave acid 6 (14.6 mg, 67%) as a pale yellow oil: R$_f$=0.24 (10% MeOH/CH$_2$Cl$_2$); [α]$_{25}^D$ 9.5° (c 1.05, CH$_3$OH); $^1$H NMR (700 MHz, CH$_3$OD) δ1.20 (m, 1H), 1.79-1.81 (m, 2H), 2.17 (m, 1H), 2.57 (d, J=6.9 Hz, 1H), 2.72-2.78 (dd, J=8.3, 13.6 Hz, 1H), 2.79 (t, J=2.5 Hz, 1H), 2.81 (m, 1H), 2.98-3.01 (dd, J=4.9, 13.7 Hz, 1H), 3.06-3.09 (dd, J=4.1, 14.3 Hz, 1H), 3.16 (m, 1H), 3.47-3.49 (m, 1H), 3.72 (d; J=14.5 Hz, 1H), 3.76 (d, J=14.5 Hz, 1H), 3.82-3.89 (m, 1H), 4.22-4.25 (dd, J=6.9, 10.4 Hz, 1H), 4.37-4.39 (dd, J=4.0, 11.3 Hz, 1H), 4.47-4.49 (m, 2H), 7.14 (m, 3H), 7.22 (m, 2H), 7.28 (t, J=7.4 Hz, 1H), 7.34 (m, 3H), 7.42 (m, 2H), 7.53 (d, J=7.2 Hz, 1H), 8.25 (s, 1H), 8.40 (d, J=4.8 Hz, 1H), 8.47 (s, 1H); $^{13}$C NMR (175 MHz, CH$_3$OD) δ25.1, 29.5, 33.6, 38.6, 39.8, 39.9, 47.3, 48.3, 49.8, 54.6, 62.7, 73.7, 77.4, 123.8, 126.0, 127.1, 127.9, 128.5, 129.1, 129.5, 134.4, 134.5, 137.3, 137.9, 146.9, 149.2, 160.0, 170.7, 171.0, 173.1, 173.8. HRMS m/z calculated for C$_{35}$H$_{39}$N$_6$O$_6$ [M+H]$^+$ 639.2926. found 639.2942. RP-HPLC system 1: 98.9%, t$_R$=7.96 min. RP-HPLC system 3: 98.5%, t$_R$=11.86 min.

Phenylacetyl-aza-phenylalaninyl-(2S)-prolyl-(2S)-(3-pyridyl)alaninyl-(3S)-β-homophenylalanine (7) was obtained from 22b (31 mg, 0.039 mmol) as described above in 66% yield: R$_f$=0.32 (10% MeOH/CH$_2$Cl$_2$); [α]$_{25}^D$ 12.4° (c 2.5, CH$_3$OH); $^1$H NMR (700 MHz, CH$_3$OD) δ1.16-1.23 (m, 1H), 1.79-1.83 (m, 2H), 2.18-2.20 (m, 1H), 2.61 (m, 2H), 2.79-2.82 (dd, J=8.7, 13.1 Hz, 1H), 2.86-2.90 (m, 1H), 3.02 (d, J=10.9 Hz, 1H), 3.12 (d, J=12.7 Hz, 1H), 3.17-3.21 (dd, J=9.8, 17.1 Hz, 1H), 3.48 (m, 1H), 3.61 (s, 2H), 3.93 (m, 1H), 4.28-4.31 (dd, J=6.9, 10.6 Hz, 1H), 4.41 (d, J=7.9 Hz, 1H), 4.52 (m, 1H), 5.11 (m, 1H), 7.17-7.18 (m, 3H), 7.21 (m, 2H), 7.28-7.37 (m, 11H), 7.59 (s, 1H), 8.31 (s, 1H), 8.42 (s, 1H); $^{13}$C NMR (175 MHz, CH$_3$OD) δ25.2, 29.4, 29.5, 33.6, 39.8, 40.0, 48.4, 50.0, 54.0, 54.6, 62.9, 126.1, 127.1, 127.5, 128.0, 128.3, 128.5, 129.1, 129.2, 129.5, 134.4, 135.9, 138.1, 161.0, 170.7, 170.8, 173.3. HRMS m/z calculated for C$_{39}$H$_{43}$N$_6$O$_6$ [M+H]$^+$ 691.3238. found 691.3231. RP-HPLC system 1: 97.4%, t$_R$=8.84 min. RP-HPLC system 3: 98.9%, t$_R$=13.99 min.

Phenylacetyl-aza-allylglycinyl-(2S)-prolyl-(2S)-(3-pyridyl)alaninyl-(3S)-β-homophenylalanine (8) was obtained from 22c (18 mg, 0.025 mmol) as described above in 72% yield: R$_f$=0.28 (10% MeOH/CH$_2$Cl$_2$); [α]$_{25}^D$ −54.2° (c 1.2, CH$_3$OH); $^1$H NMR (700 MHz, CH$_3$OD) δ1.18 (m, 1H), 1.77-1.82 (m, 2H), 2.17-2.28 (m, 1H), 2.57 (m, 2H), 2.73-2.76 (dd, J=8.9, 13.4 Hz, 1H), 2.81-2.87 (m, 1H), 2.98-3.02 (dd, J=3.7, 13.5 Hz, 1H), 3.06-3.08 (d, J=12.5 Hz, 1H), 3.16-3.20 (q, J=5.8 Hz, 1H), 3.48 (m, 1H), 3.64 (br, 1H), 3.67 (d, J=14.4 Hz, 1H), 3.70 (d, J=14.5 Hz, 1H), 4.24-4.27 (dd, J=6.9, 10.5 Hz, 1H), 4.38 (d, J=7.8 Hz, 2H), 4.49 (m, 1H), 5.15 (dd, J=1.0, 17.2 Hz, 1H), 5.21-5.23 (d, J=10.2 Hz, 1H), 5.88-5.92 (m, 1H), 7.16 (m, 3H), 7.24-7.28 (m, 3H), 7.32-7.34 (m, 3H), 7.38 (m, 2H), 7.56 (s, 1H), 8.29 (s, 1H), 8.40 (s, 1H); $^{13}$C NMR (175 MHz, CH$_3$OD) δ25.2, 29.5, 39.9, 40.1, 48.4, 49.9, 53.2, 54.6, 62.7, 118.8, 126.0, 127.1, 127.9, 128.4, 129.1, 129.4, 132.6, 134.4, 138.1, 161.0, 170.7, 170.8, 173.3. HRMS m/z calculated for C$_{35}$H$_{41}$N$_6$O$_6$ [M+H]$^+$ 641.3082. found 641.3086. RP-HPLC system 1: 95.8%, t$_R$=8.20 min. RP-HPLC system 3: 98.7%, t$_R$=12.68 min.

Phenylacetyl-aza-alaninyl-(2S)-prolyl-(2S)-(3-pyridyl)alaninyl-(3S)-β-homophenylalanine (9) was obtained from ester 22d (16.7 mg, 0.024 mmol) as described above in 85% yield: R$_f$=0.21 (10% MeOH/CH$_2$Cl$_2$); [α]$_{25}^D$ −100° (c 1.1, CH$_3$OH); $^1$H NMR (700 MHz, CH$_3$OD) δ1.13-1.19 (m, 1H), 1.75-1.80 (m, 2H), 2.16-2.18 (m, 1H), 2.60 (m, 2H), 2.72-2.75 (dd, J=8.9, 13.4 Hz, 1H), 2.80-2.82 (m, 1H), 2.97-2.99 (dd, J=4.5, 13.6 Hz, 1H), 3.05 (s, 3H), 3.06 (s, 1H), 3.10-3.14 (m, 1H), 3.45 (t, J=8.7 Hz, 1H), 3.70 (d, J=14.6 Hz, 1H), 3.71 (d, J=14.5 Hz, 1H), 4.22-4.25 (dd, J=6.8, 10.7 Hz, 1H), 4.36-4.39 (dd, J=3.6, 11.2 Hz, 1H), 4.49 (m, 1H), 7.12-7.18 (m, 3H), 7.20-7.29 (m, 3H), 7.32-7.34 (m, 3H), 7.38-7.41 (m, 2H), 7.57 (s, 1H), 8.25 (s, 1H), 8.48 (s, 1H); $^{13}$C NMR (175 MHz, CH$_3$OD) δ29.5, 30.8, 33.5, 37.8, 39.9, 40.2, 48.3, 49.8, 54.5, 62.8, 123.8, 126.0, 127.1, 127.9, 128.5, 128.9, 129.0, 129.2, 129.4, 134.4, 134.6, 137.3, 138.0, 146.8, 149.1, 161.1, 170.6, 170.7, 173.3. HRMS m/z calculated for C$_{33}$H$_{39}$N$_6$O$_6$ [M+H]$^+$ 615.2926. found 615.2937. RP-HPLC system 1: 98.6%, t$_R$=7.78 min. RP-HPLC system 3: 99%, t$_R$=11.58 min.

Myometrial Contraction Assay

Ex vivo myometrial contraction assays were performed as previously described[24]. Briefly, uteri from mice were obtained from animals immediately after delivery. Myometrial strips (2-3 mm wide and 1-2 cm long) were suspended in organ baths containing Krebs buffer equilibrated with 21% oxygen at 37° C. with an initial tension, as well as peak, duration, and frequency of spontaneous contractions in the absence or in presence of PGF2α and PDC113.824 or mimic 1-9 were recorded with a Kent digital polygraph system.

ERK1/2 MAP Kinase Activation

PGF2α was obtained from Cayman. Mouse monoclonal anti-p-ERK and rabbit polyclonal anti-total ERK antibodies were from Cell Signaling. HEK293 cells stably transfected with HA-FP (HA-FP cells)[24] were employed to measure activation of MAP kinase by PGF2α using conventional western blot methods. Briefly, HA-FP cells in 6-well plates were starved for 30 min and pre-treated with 1 μM of an azapeptide (6-9) for 30 min, and then challenged with PGF2α (0.1 μM or 1 μM) for 5 min. Cells were lysed in Laemmli buffer 2× (250 mM Tris-HCl pH 6.8, 2% SDS, 10% Glycerol, 0.01% Bromophenol blue). Lysates were electrophoresed on a 10% SDS-PAGE gels, transferred to nitrocellulose membranes, and probed using mouse anti-p-ERK1/2 and rabbit anti-total-ERK1/2 antibodies. Blots were quantified by densitometry and statistical tests were performed as described.[24]

Cell Ruffling

Cell ruffling was performed as described.[24] Briefly, serum-starved FP cells plated on cover slips were pre-treated or not with PDC113.824 or azapeptide (5-9) for 30 min at 37° C., then stimulated with 1 µM PGF2α for 30 min, fixed with 4% paraformaldehyde (PFA), and stained with Fluor488™-Phalloidin. Nine fields (50-75 cells/field) per cover slip were quantified to assess circular cellular ruffling.

Example 3

Effects of PDC113.824 and Compounds 1-9 on Myometrial Contraction

Figure 7A:
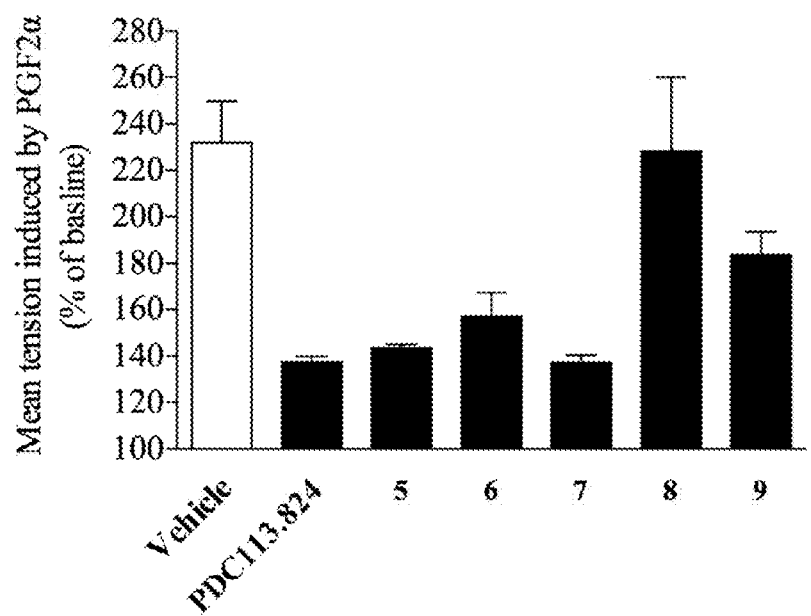
FIGS. 7A and 7B show the effects of PDC113.824 and azapeptides 5-9 on mean tension in myometrial preparations induced by PGF2α. At the beginning of each experiment, mean tension of spontaneous myometrial contraction was considered as the basal response.
Figure 7B:
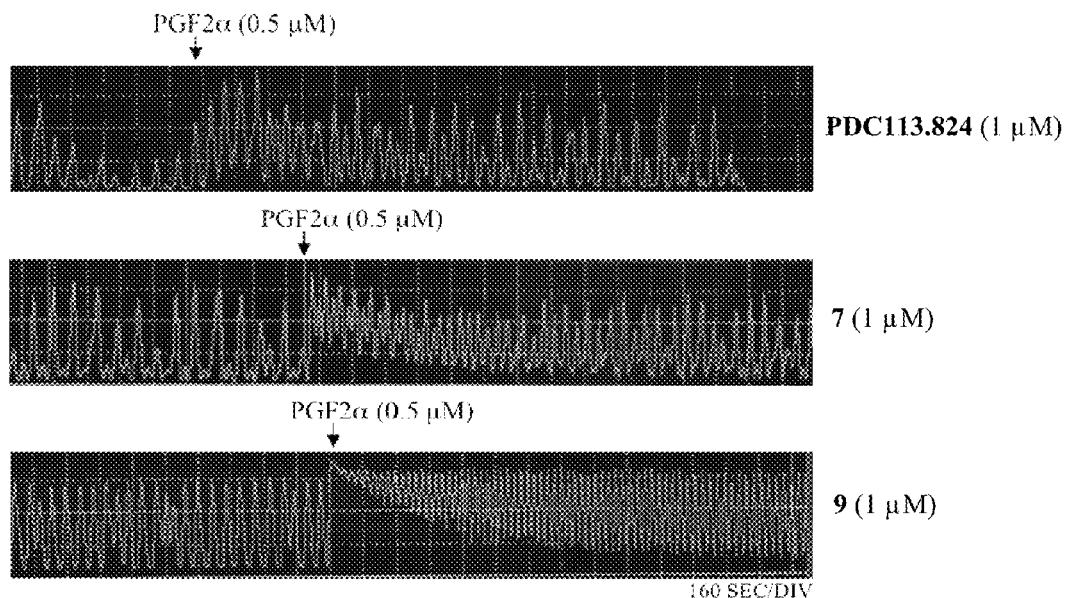

The effect of compounds 1-9 on PGF2α-induced myometrial contractions was examined to evaluate their potential to serve as tocolytics. Despite the activity of PDC113.824, none of the related azabicyclo[X.Y.0]alkanone amino acid analogs 1-4 reduced PGF2α-induced myometrial contractions.[48,49] On the other hand, azapeptides 5-9 exhibited varying degrees of activity in the myometrial contraction assay, contingent on the nature of the aza-amino acid side chain. In particular, the aza-glycine, aza-propargylglycine and aza-phenylalanine analogs 5-7, all reduced PGF2α-induced myometrial contractions with similar efficacy as PDC113.824 (FIG. 7A). Traces for the active analogs PDC113.824 and aza-phenylalanine mimic 7 are juxtaposed against that of aza-alanine analog 9 to indicate the manner by which the different analogs influence the myometrium (FIG. 7B).

Figure 8A:
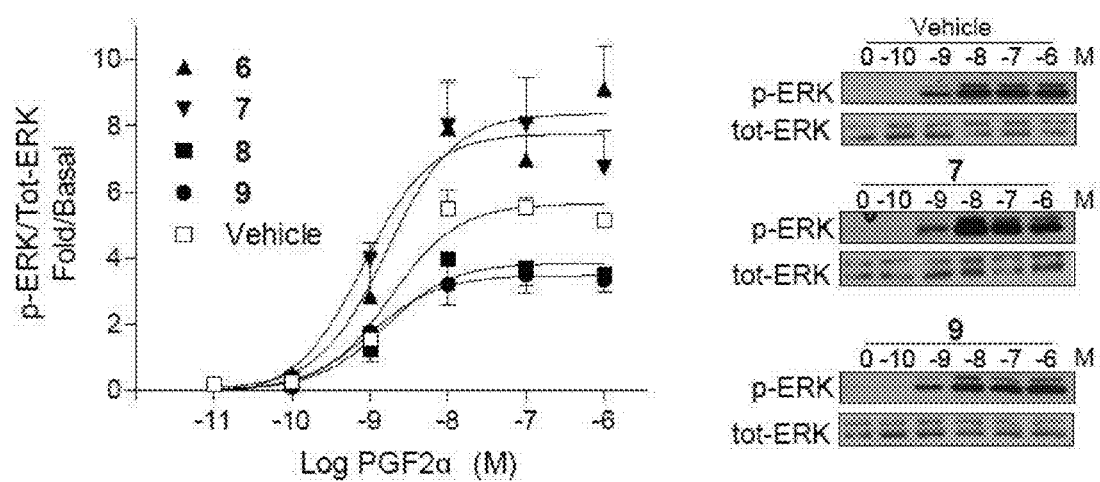
FIG. 8A shows the effects of azapeptides 6-9 on PGF2α-mediated ERK1/2 activation. PGF2α receptor (FP) expressing cells were serum-starved and pre-treated with 1 μM azapeptides (6-9) for 30 min and then stimulated with 0.1 μM (A) or 1 μM (B) PGF2α for 5 min as described.[24] Blots were quantified by densitometry and plotted compared to the non-stimulated (NS) condition. Results are representative of five independent experiments.
Figure 8B:
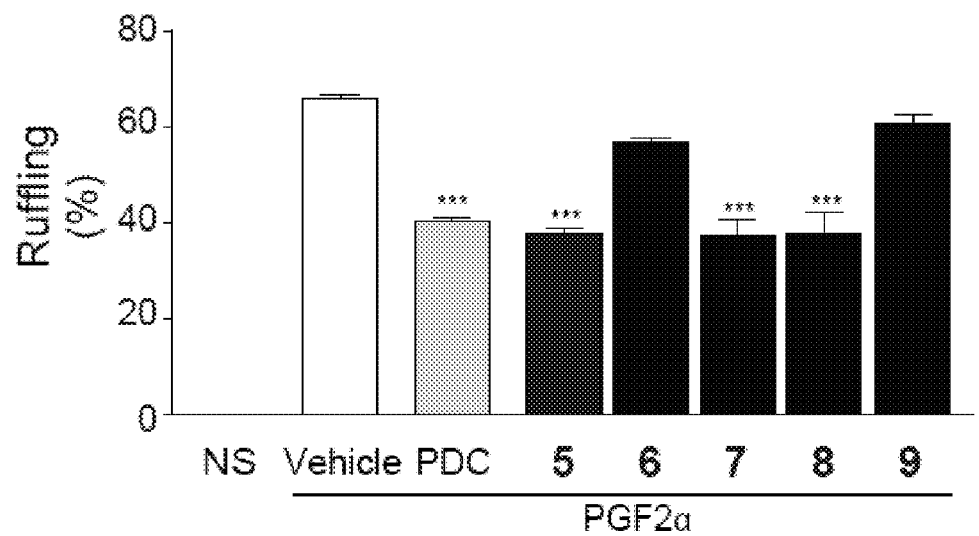
FIG. 8B shows the effects of PDC113.824 (PDC) and azapeptides 5-9 on cell ruffling in HEK293 cells. FP expressing cells seeded onto cover-slips were pretreated with PDC113.824 or azapeptide (5-9) (1 μM, 30 min) and then stimulated with PGF2α (1 μM, 30 min) as previously described.[24] Cells were then fixed with paraformaldehyde (4%), stained with Phalloidin-Alexa Fluor™488, and mounted onto cover-slips using GelTol™ media. Numbers of cells exhibiting circular ruffling under each condition were counted. Results represent mean±SEM of 3 independent experiments where more than 100 cells were counted. ***, p<0.001 are values compared to the control non-stimulated conditions.

The azapeptides were then examined for their potential to modulate PGF2α-dependent signaling, more particularly $G_q$-mediated signaling via PKC/ERK1/2 and $G_{12}$-mediated RhoA/ROCK signaling.[24] Treatment of FP cells with the azapeptide (1 µM, 30 min) in the absence of PGF2α had no effect on ERK1/2 activation or membrane ruffling (a marker of RhoA/ROCK signaling). On the other hand, pretreatment of FP cells with an azapeptide (6-9) followed by PGF2α significantly potentiated (azapeptides 6 and 7) or hindered (azapeptides 8 and 9) ERK1/2 signaling relative to cells stimulated with PGF2α alone (vehicle, FIGS. 8A and 9). Stimulation with PGF2α (1 µM, 30 min) caused membrane ruffle formation in 65.7+1.6% of FP cells (FIGS. 8B and 9). The azapeptides 5, 7 and 8 were as effective as PDC113.824 in inhibiting FP-induced cell ruffling, whereas the azapeptides 6 and 9 slightly reduced PGF2α-mediated cell ruffling.

Example 4

Effects of PDC113.824 and azapeptides 5-9 on Colorectal Cancer Cells

Figure 10:
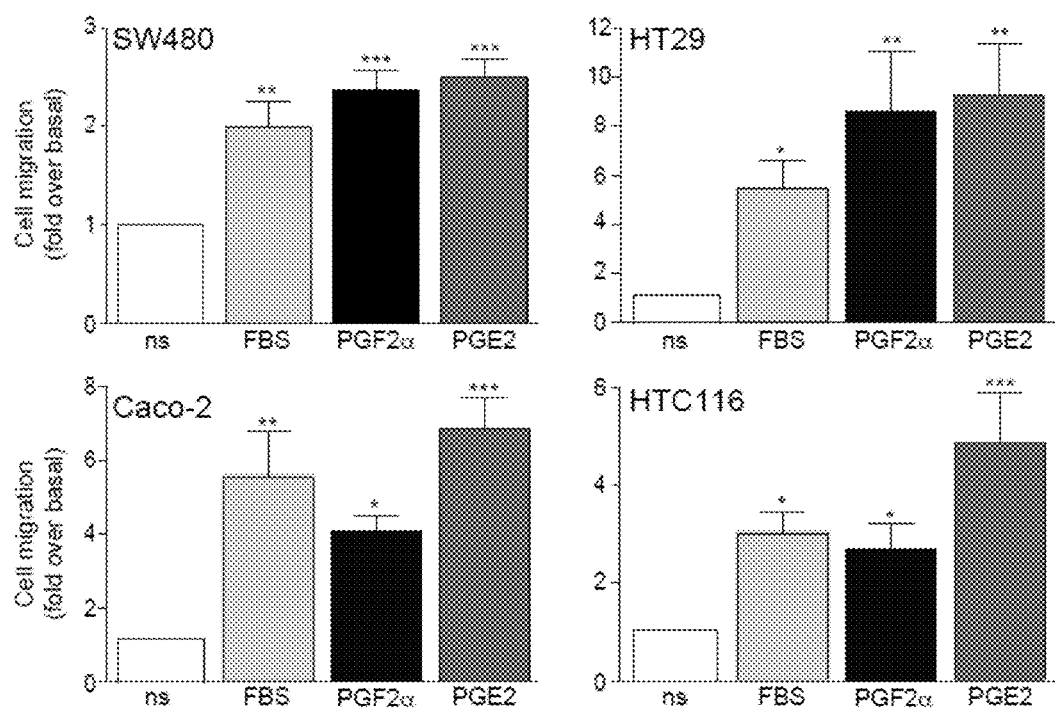
FIG. 10 shows the effect of PGF2α on colorectal cancer cell migration. SW480 (p53 mut, K-Ras mut, APC mut), HT29 (p53 mut, K-Ras WT, APC mut), Caco-2 (p53 mut, K-Ras WT, APC mut), and HTC116 (p53 mut, K-Ras mut, APC mut) cells were re-seeded into Boyden chambers coated with collagen, stimulated or not with FBS (10%), PGF2α (1

It was next tested whether PGF2α and PGE2 stimulation modulate the migration of different human colorectal adenocarcinoma cell lines. As illustrated in FIG. 10, both mediators enhanced migration of the four (4) cell lines examined in a collagen-coated Boyden chamber assay. PGF2α was as potent as PGE2 in both SW480 and HT29 cells. Next, the effect of PDC113.824 on PGF2α- and PGE2-induced cell migration was assessed using SW480 cells. In the absence of PGF2α and PGE2, PDC113.824 did not affect the migration of SW480 cells (FIG. 11). However a 30 min pre-treatment with PDC113.824 significantly blocked PGF2α-induced migration without affecting migration induced by PGE2, demonstrating that PDC113.824 acts specifically on endogenously expressed FP (FIG. 11). PGF2α-dependent remodeling of the actin cytoskeleton leading to cell migration was dependent upon activation of the Rho/ROCK signaling pathway (FIG. 12). Finally, FIG. 13 shows that pre-treatment with azapeptides 5, 7 and 8 significantly impaired the ability of SW480 cells to migrate. Pre-treatment of the cells with azapeptide 6 had an effect on cell migration but was not as effective as the others, and azapeptide 9 exhibited a relatively lower effect.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

REFERENCES (1) Slattery, M. M.; Morrison, J. J. Preterm delivery. *Lancet* 2002, 360, 1489-1497.
(2) Goldenberg, R. L.; Culhane, J. F.; Iams, J. D.; Romero, R. Preterm birth 1—Epidemiology and causes of preterm birth. *Lancet* 2008, 371, 75-84.
(3) Martin, J. A.; Kochanek, K. D.; Strobino, D. M.; Guyer, B.; MacDorman, M. F. Annual summary of vital statistics—2003. *Pediatrics* 2005, 115, 619-634.
(4) Russell, R. B.; Green, N. S.; Steiner, C. A.; Meikle, S.; Howse, J. L.; Poschman, K.; Dias, T.; Potetz, L.; Davidoff, M. J.; Damus, K.; Petrini, J. R. Cost of hospitalization for preterm and low birth weight infants in the United States. *Pediatrics* 2007, 120, E1-E9.
(5) McCormick, M. C. The contribution of low birth-weight to infant-mortality and childhood morbidity. *N. Engl. J. Med.* 1985, 312, 82-90.
(6) Hack, M.; Klein, N.; Flannery, D. J. Outcomes in young adulthood for very-low-birth-weight infants—Reply. *N. Engl. J. Med.* 2002, 347, 142-142.
(7) Robertson, P. A.; Sniderman, S. H.; Laros, R. K.; Cowan, R.; Heilbron, D.; Goldenberg, R. L.; Iams, J. D.; Creasy, R. K. Neonatal morbidity according to gestational-age and birth-weight from 5 tertiary care centers in the United-States, 1983 through 1986 *Am. J. Obstet. Gynecol.* 1992, 166, 1629-1645.
(8) Rich-Edwards, J. W.; Stampfer, M. J.; Manson, J. E.; Rosner, B.; Hankinson, S. E.; Colditz, G. A.; Willett, W. C.; Hennekens, C. H. Birth weight and risk of cardiovascular disease in a cohort of women followed up since 1976. *British Medical Journal* 1997, 315, 396-400.
(9) Iams, J. D.; Romero, R.; Culhane, J. F.; Goldenberg, R. L. Preterm birth 2—Primary, secondary, and tertiary interventions to reduce the morbidity and mortality of preterm birth. *Lancet* 2008, 371, 164-175.
(10) Anotayanonth, S.; Subhedar, N. V.; Garner, P.; Neilson, J. P.; Harigopal, S. Betamimetics for inhibiting preterm labour. *Cochrane Database Syst Rev* 2004, CD004352.
(11) Mittendorf, R.; Covert, R.; Boman, J.; Khoshnood, B.; Lee, K. S.; Siegler, M. Is tocolytic magnesium sulphate associated with increased total paediatric mortality? *Lancet* 1997, 350, 1517-1518.

(12) Papatsonis, D.; Flenady, V.; Cole, S.; Liley, H. Oxytocin receptor antagonists for inhibiting preterm labour. *Cochrane Database Syst Rev.* 2005.

(13) Goodwin, T. M.; Valenzuela, G.; Silver, H.; Hayashi, R.; Creasy, G. W.; Lane, R. Treatment of preterm labor with the oxytocin antagonist atosiban. *Am. J. Perinatol.* 1996, 13, 143-146.

(14) Duchateau, F. X.; Max, A.; Harscoat, S.; Curac, S.; Ricard-Hibon, A.; Mantz, J. Comparison between atosiban and nicardipine in inducing hypotension during in-utero transfers for threatening premature delivery. *Eur. J. Emerg. Med.* 2010, 17, 142-145.

(15) King, J. F.; Flenady, V.; Papatsonis, D.; Dekker, G.; Carbonne, B. Calcium channel blockers for inhibiting preterm labour; a systematic review of the evidence and a protocol for administration of nifedipine. *Aust. N. Z. J. Obstet. Gynaecol.* 2003, 43, 192-198.

(16) Coomarasamy, A.; Knox, E. M.; Gee, H.; Song, F. J.; Khan, K. S. Effectiveness of nifedipine versus atosiban for tocolysis in preterm labour: a meta-analysis with an indirect comparison of randomised trials. *Bjog* 2003, 110, 1045-1049.

(17) Higby, K.; Xenakis, E. M. J.; Pauerstein, C. J.; Harbert, G. M.; Jones, H.; Merkatz, I. R.; Creasy; Woods, J.; Cefalo, R. C.; Gibbs, R. S.; Scott, S.; Queenan, J. T.; Kirschbaum; Nelson, K. Do tocolytic agents stop preterm labor—a critical and comprehensive review of efficacy and safety *Am. J. Obstet. Gynecol.* 1993, 168, 1247-1259.

(18) Haas, D. M.; Imperiale, T. F.; Kirkpatrick, P. R.; Klein, R. W.; Zollinger, T. W.; Golichowski, A. M. Tocolytic Therapy—A Meta-Analysis and Decision Analysis. *Obstetrics and Gynecology* 2009, 113, 585-594.

(19) Marshall, C. The art of induction/augmentation of labor. *J Obstet Gynecol Neonatal Nurs* 1985, 14, 22-8.

(20) Olson, D. M. The role of prostaglandins in the initiation of parturition. *Best Practice & Research in Clinical Obstetrics & Gynaecology* 2003, 17, 717-730.

(21) Brodt-Eppley, J.; Myatt, L. Prostaglandin receptors in lower segment myometrium during gestation and labor. *Obstetrics and Gynecology* 1999, 93, 89-93.

(22) Sugimoto, Y.; Segi, E.; Tsuboi, K.; Ichikawa, A.; Narumiya, S. Female reproduction in mice lacking the prostaglandin F receptor—Roles of prostaglandin and oxytocin receptors in parturition. In *Vasopressin and Oxytocin—Molecular, Cellular, and Clinical Advances*, Zingg, H. H.; Bourque, C. W.; Bichet, D. G., Eds. Plenum Press Div Plenum Publishing Corp: New York, 1998; Vol. 449, pp 317-321.

(23) Sugimoto, Y.; Yamasaki, A.; Segi, E.; Tsuboi, K.; Aze, Y.; Nishimura, T.; Oida, H.; Yoshida, N.; Tanaka, T.; Katsuyama, M.; Hasumoto, K.; Murata, T.; Hirata, M.; Ushikubi, F.; Negishi, M.; Ichikawa, A.; Narumiya, S. Failure of parturition in mice lacking the prostaglandin F receptor. *Science* 1997, 277, 681-683.

(24) Goupil, E.; Tassy, D.; Bourguet, C.; Quiniou, C.; Wisehart, V.; Petrin, D.; Le Gouill, C.; Devost, D.; Zingg, H. H.; Bouvier, M.; Saragovi, H. U.; Chemtob, S.; Lubell, W. D.; Claing, A.; Hebert, T. E.; Laporte, S. A. A Novel Biased Allosteric Compound Inhibitor of Parturition Selectively Impedes the Prostaglandin F2 alpha-mediated Rho/ROCK Signaling Pathway. *J. Biol. Chem.* 2010, 285, 25624-25636.

(25) Presland, J. Identifying novel modulators of G protein-coupled receptors via interaction at allosteric sites. *Current Opinion in Drug Discovery & Development* 2005, 8, 567-576.

(26) Kenakin, T. P. Ligand Detection in the Allosteric World. *J. Biomol. Screen* 2010, 15, 119-130.

(27) Peri, K. G.; Quiniou, C.; Hou, X.; Abran, D.; Varma, D. R.; Lubell, W. D.; Chemtob, S. THG113: A novel selective FP antagonist that delays preterm labor. *Seminars in Perinatology* 2002, 26, 389-397.

(28) Peri, K.; Polyak, F.; Lubell, W.; Thouin, E.; Chemtob, S. Peptides and peptidomimetics useful for inhibiting the avtivity of prostaglandin F2a receptor WO/2003/104266.

(29) Hirst, J. J.; Parkington, H. C.; Young, I. R.; Palliser, H. K.; Peri, K. G.; Olson, D. M. Delay of preterm birth in sheep by THG113.31, a prostaglandin F-2 alpha receptor antagonist. *Am. J. Obstet. Gynecol.* 2005, 193, 256-266.

(30) Hummel, G.; Reineke, U.; Reimer, U. Translating peptides into small molecules. *Mol Biosyst* 2006, 2, 499-508.

(31) Vlieghe, P.; Lisowski, V.; Martinez, J.; Khrestchatisky, M. Synthetic therapeutic peptides: science and market. *Drug Discovery Today* 2010, 15, 40-56.

(32) Edwards, C. M. B.; Cohen, M. A.; Bloom, S. R. Peptides as drugs. *Qjm—an International Journal of Medicine* 1999, 92, 1-4.

(33) Lombart, H. G.; Lubell, W. D. Rigid dipeptide mimetics: Efficient synthesis of enantiopure indolizidinone amino acids. *J. Org. Chem.* 1996, 61, 9437-9446.

(34) Halab, L.; Becker, J. A. J.; Darula, Z.; Tourwe, D.; Kieffer, B. L.; Simonin, F.; Lubell, W. D. Probing opioid receptor interactions with azacycloalkane amino acids. Synthesis of a potent and selective ORL1 antagonist. *J. Med. Chem.* 2002, 45, 5353-5357.

(35) Polyak, F.; Lubell, W. D. Rigid dipeptide mimics: Synthesis of enantiopure 5- and 7-benzyl and 5,7-dibenzyl indolizidinone amino acids via enolization and alkylation of delta-oxo alpha,omega-di-N-(9-(9-phenylfluorenyl)) amino azelate esters. *J. Org. Chem.* 1998, 63, 5937-5949.

(36) Gosselin, F.; Lubell, W. D. Rigid dipeptide surrogates: Syntheses of enantiopure quinolizidinone and pyrroloazepinone amino acids from a common diaminodicarboxylate precursor. *J. Org. Chem.* 2000, 65, 2163-2171.

(37) Gosselin, F.; Lubell, W. D. An Olefination Entry for the Synthesis of Enantiopure a,w-Diamino-dicarboxylates and Azabicyclo[X.Y.0]alkane Amino Acids. *J. Org. Chem.* 1998, 63, 7463-7471.

(38) DeGrado, W. F.; Kaiser, E. T. Polymer-bound oxime esters as supports for solid-phase peptide synthesis. The preparation of protected peptide fragments *J. Org. Chem.* 1980, 45, 1295-1300.

(39) Kaiser, E. T.; Mihara, H.; Laforet, G. A.; Kelley, J. W.; Walters, L.; Findeis, M. A.; Sasaki, T. Peptide and protein synthesis by segment synthesis-condensation. *Science* 1989, 243, 188-192.

(40) Andre, F.; Boussard, G.; Bayeul, D.; Didierjean, C.; Aubry, A.; Marraud, M. Aza-peptides 2. X-ray structures of aza-alanine and aza-asparagine-containing peptides. *J. Peptide Res.* 1997, 49, 556-562.

(41) Lee, H. J.; Ahn, I. A.; Ro, S.; Choi, K. H.; Choi, Y. S.; Lee, K. B. Role of azamino acid residue in beta-turn formation and stability in designed peptide. *J. Peptide Res.* 2000, 56, 35-46.

(42) Lee, H. J.; Choi, K. H.; Ahn, I. A.; Ro, S.; Jang, H. G.; Choi, Y. S.; Lee, K. B. The beta-turn preferential solution conformation of a tetrapeptide containing an azamino acid residue. *Journal of Molecular Structure* 2001, 569, 43-54.

(43) Thormann, M.; Hofmann, H. J. Conformational properties of azapeptides. *Journal of Molecular Structure-Theochem* 1999, 469, 63-76.

(44) Boeglin, D.; Hamdan, F. F.; Melendez, R. E.; Cluzeau, J.; Laperriere, A.; Heroux, M.; Bouvier, M.; Lubell, W. D.

Calcitonin gene-related peptide analogues with aza and indolizidinone amino acid residues reveal conformational requirements for antagonist activity at the human calcitonin gene-related peptide 1 receptor. *Journal of Medicinal Chemistry* 2007, 50, 1401-1408.

(45) Bourguet, C. B.; Sabatino, D.; Lubell, W. D. Benzophenone Semicarbazone Protection Strategy for Synthesis of Aza-Glycine Containing Aza-Peptides. *Biopolymers, Peptide Science* 2008, 90, 824-831.

(46) Bourguet, C. B.; Proulx, C.; Klocek, S.; Sabatino, D.; Lubell, W. D. Solution-phase submonomer diversification of aza-dipeptide building blocks and their application in aza-peptide and aza-DKP synthesis. *Journal of Peptide Science* 2010, 16, 284-296.

(47) Sabatino, D.; Proulx, C.; Klocek, S.; Bourguet, C. B.; Boeglin, D. Ong, H.; Lubell, W. D. Exploring Side-Chain Diversity by Submonomer Solid-Phase Aza-Peptide Synthesis *Org. Lett.* 2009, 11, 3650-3653.

(48) Bourguet, C. B.; Hou, X.; Chemtob, S.; Lubell, W. D. Influence of Peptide Mimic Turn Stereochemistry on Allosteric Antagonism at the Prostaglandin F2α Receptor In *Peptides* 2006, *Proceedings of the 29th European Peptide Symposium*, K. Rolka, P. Rekowski, J. Silberring Editors, 2006, 436-437.

(49) Bourguet, C. B.; Hou, X.; Chemtob, S.; Lubell, W. D. Exploring the relationship between turn geometry and allosteric antagonism of peptide mimic ligands for the prostaglandin F2alpha receptor, Peptides for Youth, The Proceedings of the 20th American Peptide Symposium, Advances in Experimental Medicine and Biology Volume 611, S. E. Del Valle, E. Escher, W. D. Lubell, Editors, Springer Science, New York, 2009, pp. 271-273.

(50) Linder, M. R.; Steurer, S.; Podlech, J. (S)-3-(tert-Butyloxycarbonylamino)-4-phenylbutanoic acid. *Organic Syntheses* 2002, 79, 154.

The invention claimed is:

1. A prostaglandin-F2α (PGF2α) receptor (FP) modulator of formula

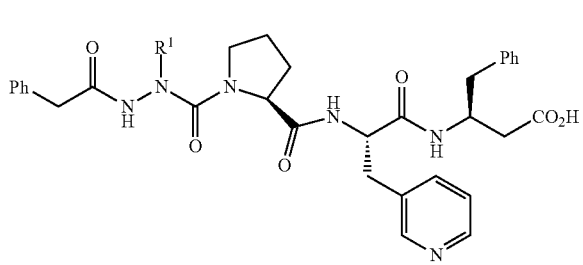

wherein $R^1$ is H, $CH_3$, $CH_2CCH$, $CH_2CHCH_2$ or $CH_2Ph$.

2. The FP modulator of claim 1, wherein $R^1$ is H.
3. The FP modulator of claim 1, wherein $R^1$ is $CH_3$.
4. The FP modulator of claim 1, wherein $R^1$ is $CH_2CCH$.
5. The FP modulator of claim 1, wherein $R^1$ is $CH_2CHCH_2$.
6. The FP modulator of claim 1, wherein $R^1$ is $CH_2Ph$.
7. A pharmaceutical composition comprising the FP modulator of claim 1 and a pharmaceutically acceptable excipient.

* * * * *